US006664282B2

(12) United States Patent
ElAbdellaoui et al.

(10) Patent No.: US 6,664,282 B2
(45) Date of Patent: Dec. 16, 2003

(54) SYNTHESIS OF [3,5,7]-1H-IMIDAZO [1,5-A] IMIDAZOL-2 (3H)- ONE COMPOUNDS

(75) Inventors: Hassan M. ElAbdellaoui, San Diego, CA (US); John M. Ostresh, Encinitas, CA (US); Richard A. Houghten, Solano Beach, CA (US)

(73) Assignee: Torrey Pines Institute for Molecular Studies, San Diego, CA (US)

( * ) Notice: Subject to any disclaimer, the term of this patent is extended or adjusted under 35 U.S.C. 154(b) by 16 days.

(21) Appl. No.: 10/141,439

(22) Filed: May 8, 2002

(65) Prior Publication Data

US 2002/0193608 A1 Dec. 19, 2002

Related U.S. Application Data

(62) Division of application No. 09/659,370, filed on Sep. 12, 2000.
(60) Provisional application No. 60/154,443, filed on Sep. 17, 1999.

(51) Int. Cl.$^7$ ..................... A61K 31/415; C07D 403/02

(52) U.S. Cl. ................... 514/393; 548/303.1; 435/6
(58) Field of Search ................. 548/303.1; 514/393; 435/4, DIG. 34, 6

(56) References Cited

U.S. PATENT DOCUMENTS

| 4,478,845 A | 10/1984 | Whitney |
| 5,194,392 A | 3/1993 | Geysen |
| 5,541,061 A | 7/1996 | Fodor et al. |
| 5,556,762 A | 9/1996 | Pinilla et al. |
| 5,990,145 A | 11/1999 | Wehner et al. |

FOREIGN PATENT DOCUMENTS

| EP | 854140 | 12/1997 |
| EP | 854145 | 12/1997 |
| WO | WO 98/34113 | 8/1998 |
| WO | WO 98/41223 | 9/1998 |

OTHER PUBLICATIONS

Birkett, P. R.; Chapleo, C. B.; MacKenzie, G. "Synthesis and intramolecular cyclization of 5–aminoimidazolealkanoates and their conversion to purine derivatives" Synthesis 1991, 2, 157–159 * Note: this is IDS reference A9.*
S.H. Baek, et al., "Identification of the Peptides that Stimulate the Phosphoinositide Hydrolysis in Lymphocyte Cell Lines from Peptide Libraries," *J. of Biol. Chem.*, 271(14):8170–8175 (1996).
E. Bianchi, et al., "A Conformationally Homogeneous Combinatorial Peptide Library," 1995 *Academic Press Limited*, pp. 154–160, Accepted Dec. 23, 1994.
Birkett, et al., "Synthesis and Intramolecular Cyclisation of 5–Aminoimidazolealkanoates and Their Conversion to Purine Derivatives," *Synthesis*, 157–59 (1991).

B. Déprez, et al., "Orthogonal Combinatorial Chemical Libraries," *J. Am. Chem. Soc.* 117:5404–5406 (1995).
B. Fleckenstein, et al., "New Ligands Binding to the Human Leukocyte Antigen Class II Molecule DRBI*0101 Based on the Activity Pattern of an Undecapeptide Library," *Eur. J. Biochem.*, 240:71–77 (1996).
S.P.A. Fodor, et al., "Light–Directed, Spatially Addressable Parallel Chemical Synthesis," *Science*, 251:767–778 (1991).
B.R. Gundlach, et al., "Specificity and Degeneracy of Minor Histocompatability Antigen–Specific MHC–Restricted CTL." *J. Immunol.* 156:3645–3651 (1996).
B.R. Gundlach, et al., "Determination of T Cell Epitopes with Random Peptide Libraries," *J. Immunol. Methods* 192:149–155 (1996).
B. Hemmer, et al., "Identification of High Potency Microbial and Self Ligands for a Human Autoreactive Class II–Restricted T Cell Clone," *J. Exp. Med* 185(9):165–169 (1997).
R.A. Lahti, et al., "[$^3$H]U–69593 A Highly Selective Ligand for the Opoid $_K$ Receptor," *European J. Pharmacol.* 109:281–284 (1985).
R.A. Lahti, et al., "Properties of a Selective Kappa Agonist, U–50, 488H," *Life Sci.* 31(20&21):2257–2260 (1982).
J.Y. Park, et al., "Identification of the Peptides that Inhibit the Stimulation of Thyrotropin Receptor by Graves' Immunoglobin G from Peptide Libraries," *Endocrinology*, 138(2):617–626 (1997).
A.F. Spatola, et al., "Rediscovering an Endothelin Antagonist (BQ–123): A Self–Deconvoluting Cyclic Pentapeptide Library," *J.Med. Chem.* 39(19)3842–3846 (1996).
A. Stryhn, et al., "Peptide Binding Specificity of Major Histocompatability Complex Class I Resolved into an Array of Apparently Independent Subspecificities: Quantitation by Peptide Libraries and Improved Prediction of Binding," *Eur. J. Immonol.* 26:1911–1918 (1996).
T.A. Rano, et al., "A Combinatorial Approach for Determining Protease Specificities: Application to Interleukin–1β Converting Enzyme(ICE)," *Chemistry &Biology* 4(2):149–155 (1997).
N.A. Thornberry, et al., "A Combinatorial Approach Defines Specificities of Members of the Caspase Family and Granzyme B," *J. Biol. Chem.* 272(29):17907–17911 (1997).
P.F. Vonvoigtlander, et al., "U–50, 488: A Selective and Structurally Novel Non–Mu (Kappa) Opioid Agonist," *J.Pharmacol. Exp. Ther.* 224(1):7–12 (1983).
A. Wallace, et al., "Selection of Potent Inhibitors of Farnesyl–Protein Transferase from a Synthetic Tetrapeptide Combinatorial Library," *J. Biol. Chem.* 271(49):31306–31311 (1996).

(List continued on next page.)

*Primary Examiner*—Bennett Celsa
*Assistant Examiner*—Jon D. Epperson
(74) *Attorney, Agent, or Firm*—Welsh & Katz, Ltd.

(57) ABSTRACT

Individual substituted [3,5,7]-1H-imidazo[1,5-a]imidazol-2 (3H)-one compounds and their pharmaceutically-acceptable salts are disclosed, as are libraries of such compounds. Methods of preparing and using the libraries of compounds as well as individual compounds of the libraries are also disclosed.

9 Claims, No Drawings

OTHER PUBLICATIONS

A. Wallace, et al., "A Multimeric Synthetic Peptide Combinatorial Library," *Pept. Res.* 7(1):27–31 (1994).

L. Wilson–Lingardo, et al., "Deconvolution of Combinatorial Libraries for Drug Discovery: Experimental Comparison of Pooling Strategies," *J. Med. Chem.* 39:2720–2726 (1996).

Database CAS ONLINE: HCAPLUS, American Chemical Society, Washington, D.C., AN: 1970:100605, Synjic, V. et al. "Reactions of Some 1–(Carboxyalkyl Nitroimidazole Derivatives in Polyphosphoic Acid, " *J. of Heterocyclic Chem.*, 7(1):211–213 (1970) (abstract).

Rubini et al., "Synthesis of Isosteric Methylene–oxy Pseudodipeptide Analogues As Novel Amide Bond Surrogate Unites", *Tetrahedron.*, vol. 42(21), 6039–6045 (1986).

* cited by examiner

SYNTHESIS OF [3,5,7]-1H-IMIDAZO [1,5-A] IMIDAZOL-2 (3H)- ONE COMPOUNDS

CROSS-REFERENCE TO RELATED APPLICATION

This a division of allowed Application Ser. No. 09/659,370 filed on Sep. 12, 2000, that was a continuation-in-part of application Ser. No. 60/154,443, filed Sep. 17, 1999, whose disclosures are incorporated herein by reference.

TECHNICAL FIELD

The present invention relates generally to the combinatorial synthesis of [3,5,7]-1H-imidazo[1,5-a]imidazol-2 (3H)-one derivatives. More specifically, the invention provides novel [3,5,7]-1H-imidazo[1,5-a]imidazol-2(3H)-one compounds as well as novel combinatorial libraries comprised of many such compounds, and methods of synthesizing the libraries.

BACKGROUND INFORMATION

The process of discovering new therapeutically active compounds for a given indication involves the screening of all compounds from available compound collections. From the compounds tested one or more structure(s) is selected as a promising lead. A large number of related analogs are then synthesized to develop a structure-activity relation-ship and select one or more optimal compounds. With traditional one-at-a-time synthesis and biological testing of analogs, this optimization process is long and labor intensive.

Adding significant numbers of new structures to the compound collections used in the initial screening step of the discovery and optimization process cannot be accomplished with traditional one-at-a-time synthesis methods, except over a time frame of months or even years. Faster methods are needed that permit the preparation of up to thousands of related compounds in a matter of days or a few weeks. This need is particularly evident when it comes to synthesizing more complex compounds, such as the [3,5,7]-1H-imidazo[1,5-a]imidazol-2(3H)-one compounds of the present invention.

Solid-phase techniques for the synthesis of peptides have been extensively developed and combinatorial libraries of peptides have been prepared with great success. During the past four years there has been substantial development of chemically synthesized combinatorial libraries (SCLs) made up of peptides.

The preparation and use of synthetic peptide combinatorial libraries has been described for example by Dooley in U.S. Pat. No. 5,367,053; Huebner in U.S. Pat. No. 5,182,366; Appel et al in WO PCt 92/09300; Geysen in published European Patent Application 0 138 855 and Pimmg in U.S. Pat. No. 5,143,854. Such SCLs provide the efficient synthesis of an extraordinary number of various peptides in such libraries and the rapid screening of the library that identifies lead pharmaceutical peptides.

Peptides have been, and remain, attractive targets for drug discovery. Their high affinities and specificities toward biological receptors as well as the ease with which large peptide libraries can be combinatorially synthesized make them attractive drug targets. The screening of peptide libraries has led to the identification of many biologically-active lead compounds. However, the therapeutic application of peptides is limited by their poor stability and bioavailability in vivo. Therefore, there is a need to synthesize and screen compounds that can maintain high affinity and specificity toward biological receptors, while exhibiting improved pharmacological properties relative to peptides.

Combinatorial approaches have recently been extended to "organic" or non-peptide libraries.

Significantly, many biologically active compounds contain the imidazole moiety. Such compounds are conformationally constrained scaffolds, are quite common in nature and many imidazole-containing natural products have been isolated encompassing a wide range of biological activities. The imidazole ring system is of particular importance because it is present in the essential amino acid histidine. The histidine residues are found at the active site of ribonuclease and several other enzymes. Drugs such as cimetidine were designed with histamine itself as the starting point [C. R. Ganellin, in *Medicinal Chemistry*, ed. S. M. Roberts and B. J. Price, Academic Press, London, 1985, p. 93; G. J. Durant, Chem Soc. Rev., 1985, 84, 375].

Several other classes of drugs are based on the imidazole ring. 2-Nitroimidazole (azomycin) is a naturally occurring antibiotic and some synthetic nitroimidazoles are active against intestinal infections (Reviews: *Nitroimidazoles; Chemistry; Pharmacology and Clinical Applications*, eds. A. Breccia, B. Cavalleri, and G. E. Adams, Plenum Press, New York, 1982; J. H. Boyer, *Nitrazoles, VCH, Deerfield Beach, Fla.,* 1986).

Imidazole-containing moieties are found in many biologically active compounds and are known to have useful therapeutic implications. There is a need to further study and develop large numbers of [3,5,7]-1H-imidazo[1,5-a]imidazol-2(3H)-one compounds and their binding to biological receptors. These compounds of the present invention are principally derived from the synthesis of dipeptides, but the dipeptides are substantially modified. In short, they are chemically modified through, acylation and cyclization via Bischler-Naprielski reaction into the subject [3,5,7]-1H-imidazo[1,5-a]imidazol-2(3H)-one, thus providing mixtures and individual compounds of substantial diversity.

BRIEF SUMMARY OF THE INVENTION

The invention provides a rapid approach for combinatorial synthesis and screening of individual compounds and libraries of [3,5,7]-1H-imidazo[1,5-a]imidazol-2(3H)-one compounds. The present invention further provides libraries and individual compounds and their pharmaceutically-acceptable salts of Formula I. The present invention also relates to the preparation of synthetic combinatorial libraries of organic compounds and their pharmaceutically-acceptable salts of Formula I, wherein $R^1$, $R^2$ and $R^3$ have the meanings provided below.

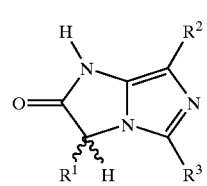

I

The present invention has several benefits and advantages. One benefit is the provision of a new synthesis for bicyclic [3,5,7]-1H-imidazo[1,5-a]imidazol-2(3H)-one compounds. The present invention provides a large array of diverse [3,5,7]-1H-imidazo[1,5-a]imidazol-2(3H)-one compounds that can be screened for biological activity, and as described below, are biologically active.

An advantage of the invention is that individual compounds can be prepared or libraries containing a plurality of compounds can be prepared.

Another benefit of the invention is that the yield of bicyclic compound produced is relatively great compared to that obtained in prior syntheses of the parental compound.

Still further benefits and advantages of the invention will be apparent to the skilled worker from the discussion that follows.

DETAILED DESCRIPTION OF THE INVENTION

The present invention relates to the preparation and use of synthetic combinatorial libraries and individual compounds of a [3,5,7]-1H-imidazo[1,5-a]imidazol-2(3H)-one also referred to as a imidazo-imidizol-one that correspond in structure to Formula I, and their pharmaceutically-acceptable salts:

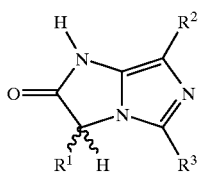

wherein:

$R^1$ and $R^2$ are independently selected from the group consisting of a hydrogen atom (hydrido), $C_1$–$C_{10}$ alkyl, $C_1$–$C_{10}$ substituted alkyl, $C_7$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group.

$R^3$ is selected from the group consisting of a hydrido, $C_1$–$C_{10}$ alkyl, $C_1$–$C_{10}$ substituted alkyl, $C_2$–$C_{10}$ alkenyl, $C_2$–$C_{10}$ substituted alkenyl, $C_2$–$C_{10}$ alkynyl, $C_2$–$C_{10}$ substituted alkynyl, $C_3$–$C_7$ substituted cycloalkyl, phenyl, $C_7$–$C_{16}$ phenylalkyl, $C_7$–$C_{16}$ phenylalkenyl, $C_7$–$C_6$ phenylalkenyl and a $C_7$–$C_{16}$ substituted phenylalkenyl group.

In one embodiment of the above bicyclic imidazo-imidizol-one of Formula I, wherein $R^1$ and $R^2$ are independently selected from the group consisting of a hydrido, methyl, benzyl, 2-butyl, aminobutyl, N,N-dimethylaminobutyl, N-methylaminobutyl, N-methyl-N-benzylaminobutyl, 2-methylpropyl, methylsulfinylethyl, methylthioethyl, N,N-dimethylaminoethyl, N,N-dimethyl-aminopropyl, N',N',N'-trimethylguanidinopropyl, N',N',N'-tribenzylguanidinopropyl, N',N'-dibenzylguanidinopropyl, N'-methylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and a 4-imidazolylmethyl substituent; and $R^3$ is selected from the group consisting of a 1-phenyl-1-cyclopropyl, 1-phenylbutyl, 2-phenylbutyl, 3-fluorobenzyl, 3-bromobenzyl, α,α,α-trifluoro-m-xylyl, p-xylyl, 4-fluorobenzyl, 3-methoxybenzyl, 4-bromobenzyl, 4-methoxybenzyl, 4-ethoxybenzyl, 4-isobutyl-a-methyl-benzyl, 3,4-dichlorobenzyl, 3,5-bis-(trifluoromethyl)-benzyl, 2-(3,4-dimethoxyphenyl)-ethyl, 4-biphenylmethyl, β-methylstyryl, 2-(trifluoromethyl)-styryl, 3,4-dimethoxybenzyl, 3,4-dihydroxybenzyl, 2-methoxystyryl, 3,4-dihydroxystyryl, 2-hydroxystyryl, phenyl, 4-chlorostyryl, 3-methoxyphenyl, 4-isopropylphenyl, 4-vinylphenyl, 4-fluorophenyl, 4-bromophenyl, 3,4-dimethoxystyryl, 4-hydroxyphenyl, trans-styryl, 3,4-dimethylphenyl, 3-fluoro-4-methylphenyl, 3-bromo-4-methyl-phenyl, 3-iodo-4-methyl-phenyl, 3,4-dichlorophenyl, 4-biphenyl, 3,4-difluorophenyl, m-tolyl, benzyl, phenethyl, 3-methoxy-4-methylphenyl, 3-phenylpropyl, 4-butylphenyl, 3,5-dimethylphenyl, 3,5-bis-(trifluoromethyl)-phenyl, 3,4-dimethoxyphenyl, 4-ethyl-4-biphenyl, 3,4,5-triethoxyphenyl, propyl, hexyl, isopropyl, 2-butyl, isobutyl, 2-pentyl, isovaleryl, 3-heptyl, 1-propenyl, 2-propenyl, trans-2-pentenyl, 1-ethyl-1-pentenyl, p-tolyl, p-anisyl, t-butyl, neopentyl, cyclohexyl, cyclohexylmethyl, dicyclohexylmethyl, cyclohexylpropyl, cycloheptyl, methyl, 2-methylcyclopropyl, cyclobutyl, cyclopentyl, cyclopentylethyl, 2-furyl, cyclohexylethyl, 4-methylcyclohexyl, 4-tert-butyl-cyclohexyl, 1-adamantyl, 4-methylcyclohexylmethyl, 1,3-pentadienyl, 2-buten-2-yl, 2-norbornanemethyl, 1-adamantanemethyl, and a 3-pentyl, 2-thiophene substituent.

In one of the preferred embodiments of the present invention, the R groups are those as immediately defined above.

In the above Formula the stereochemistry of the chiral $R^1$ group can independently be in the R or S configuration, or a mixture of the two. For instance, as will be described in further detail below, the $R^1$ group can be the side chain substituent of the α-carbon of various amino acids. The amino acids can be in the L- or D-configuration, resulting in the same R group varying only in its stereochemistry. As a consequence of an $R^1$ substituent being in one or both or two stereoconfigurations, the $R^1$ group is usually illustrated bonded to the bicyclic ring by a wavy line.

It is also noted that a compound of Formula I can exist in two tautomeric forms; i.e., in the keto or enol forms. Those two tautomeric forms are illustrated in Formula IA, below.

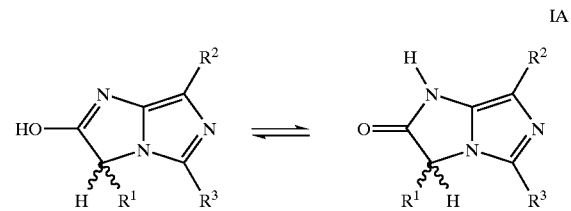

For convenience, a contemplated compound of Formula I (IA) is usually depicted and discussed as being in the keto form (imidazo-imidizol-one) with the understanding that both keto and enol forms are present in equilibrium.

Formulas of the two tautomers in both stereoconfigurations are shown below.

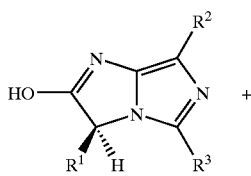

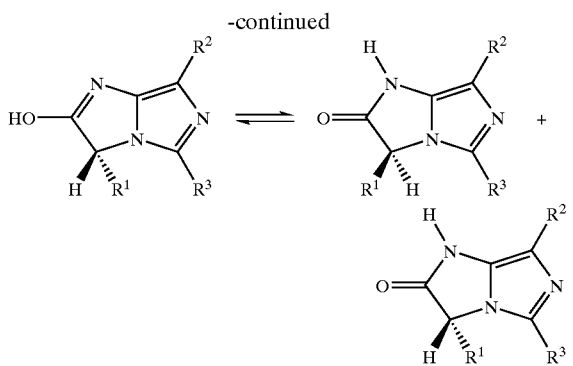

In any of the Formulas herein, the term "$C_1$–$C_{10}$ alkyl" denotes a straight or branched chain radical such as a methyl, ethyl, n-propyl, isopropyl, n-butyl, sec-butyl, tert-butyl, amyl, tert-amyl, hexyl, heptyl, decyl group and the like. The term "lower alkyl" denotes a $C_1$–$C_4$ alkyl group. A preferred "$C_1$–$C_{10}$ alkyl" group is a methyl group.

The term "$C_2$–$C_{10}$ alkenyl" denotes a radical such as a vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl and a 2-decenyl group and the like, as well as dienes and trienes of straight and branched chains containing up to ten carbon atoms and at least one carbon-to-carbon (ethylenic) double bond.

The term "$C_2$–$C_{10}$ alkynyl" denotes a radical such as ethynyl, propynyl, butynyl, pentynyl, hexynyl, heptynyl, decynyl and the like, as well as di- and triynes of straight and branched chains containing up to ten carbon atoms and at least one carbon-to-carbon (acetylenic) triple bond.

The term "$C_2$–$C_{10}$ substituted alkyl", "$C_2$–$C_{10}$ substituted alkenyl" and "$C_2$–$C_{10}$ substituted alkenyl" denote that the above $C_1$–$C_{10}$ alkyl group and $C_2$–$C_{10}$ alkenyl and alkynyl groups are substituted by one or more, and preferably one or two, halogen, hydroxy, protected hydroxy, $C_3$–$C_7$ cycloalkyl, $C_3$–$C_7$ substituted cycloalkyl, naphthyl, substituted naphthyl, adamantyl, abietyl, thiofuranyl, indolyl, substituted indolyl, amino, protected amino, (monosubstituted) amino, protected (monosubstituted) amino, (disubstituted) amino, guanidino, (monosubstituted) guanidino, (disubstituted) guanidino, (trisubstituted) guanidino, imidazolyl pyrolidinyl, $C_1$–$C_7$ acyloxy, nitro, heterocycle, substituted heterocycle, $C_1$–$C_4$ alkyl ester, carboxy, protected carboxy, carbamoyl, carbamoyloxy, carboxamide, protected carboxamide, cyano, methylsulfonylamino, methylsulfonyl, sulfhydryl, $C_1$–$C_4$ alkylthio, $C_1$–$C_4$ alkyl sulfonyl or $C_1$–$C_4$ alkoxy groups. The substituted alkyl groups can be substituted once or more, and preferably once or twice, with the same or with different substituents.

Examples of the above substituted alkyl groups include the cyanomethyl, nitromethyl, chloromethyl, hydroxymethyl, tetrahydro-pyranyloxymethyl, trityloxymethyl, propionyloxymethyl, aminomethyl, carboxymethyl, allyloxycarbonylmethyl, allylcarbonyl-aminomethyl, carbamoyloxymethyl, methoxymethyl, ethoxymethyl, t-butoxymethyl, acetoxymethyl, chloromethyl, bromomethyl, iodomethyl, 6-hydroxy-hexyl, 2,4-dichloro(n-butyl), 2-amino(isopropyl), 2-carbamoyloxyethyl chloroethyl, bromoethyl, fluoroethyl, iodoethyl, chloropropyl, bromopropyl, fluoropropyl, iodopropyl and the like.

In preferred embodiments of the subject invention, $C_1$–$C_1$ alkyl, $C_2$–$C_{10}$ alkenyl, $C_2$–$C_{10}$ alkynyl, $C_1$–$C_{10}$ substituted alkyl, $C_2$–$C_{10}$ substituted alkenyl, or $C_2$–$C_{10}$ substituted alkynyl, are more preferably $C_1$–$C_7$ or $C_2$–$C_7$, respectively, and more preferably, $C_1$–$C_6$ or $C_2$–$C_6$ as is appropriate for unsaturated substituents. However, it should be appreciated by those of skill in the art that one or a few carbons usually can be added to an alkyl, alkenyl, alkynyl, substituted or unsubstituted, without substantially modifying the structure and function of the subject compounds and that, therefore, such additions would not depart from the spirit of the invention.

The term "$C_1$–$C_4$ alkoxy" as used herein denotes groups that are ether groups containing up to four carbon atoms such as methoxy, ethoxy, n-propoxy, isopropoxy, n-butoxy, t-butoxy and like groups. A preferred $C_1$–$C_4$ alkoxy group is methoxy.

The term "$C_1$–$C_7$ acyloxy" denotes a carboxy group-containing substituent containing up seven carbon atoms such as formyloxy, acetoxy, propanoyloxy, butanoyloxy, pentanoyloxy, hexanoyloxy, heptanoyloxy, benzoyloxy and the like.

Similarly, the term "$C_1$–$C_7$ acyl" encompasses groups such as formyl, acetyl, propionoyl, butyroyl, pentanoyl, hexanoyl, heptanoyl, benzoyl and the like.

The substituent term "$C_3$–$C_7$ cycloalkyl" includes the cyclopropyl, cyclobutyl, cyclopentyl, cyclohexyl or cycloheptyl rings. The substituent term "$C_3$–$C_7$ substituted cycloalkyl" indicates an above cycloalkyl ring substituted by a halogen, hydroxy, protected hydroxy, phenyl, substituted phenyl, heterocycle, substituted heterocycle, $C_1$–$C_{10}$ alkyl, $C_1$–$C_4$ alkoxy, carboxy, protected carboxy, amino, or protected amino.

The substituent term "$C_5$–$C_7$ cycloalkenyl" indicates a substituent that is itself a 1-, 2-, or 3-substituted cyclopentenyl ring, a 1-, 2-, 3- or 4-substituted cyclohexenyl ring or a 1-, 2-, 3-,4- or 5-substituted cycloheptenyl ring, whereas the term "substituted $C_3$–$C_7$ cycloalkenyl" denotes the above $C_3$–$C_7$ cycloalkenyl rings substituted by a $C_1$–$C_{10}$ alkyl radical, halogen, hydroxy, protected hydroxy, $C_1$–$C_4$ alkoxy, carboxy, protected carboxy, amino, or protected amino.

The term "heterocyclic ring" or "heterocycle" denotes an optionally substituted 5-membered or 6-membered ring that has 1 to 4 heteroatoms, such as oxygen, sulfur and/or nitrogen, in particular nitrogen either alone or in conjunction with sulfur or oxygen ring atoms. These five-membered or six-membered rings can be fully unsaturated or partially unsaturated, with fully unsaturated rings being preferred.

Preferred heterocyclic rings include pyridino, pyrimidino, and pyrazino, furano, and thiofurano rings. The heterocyles can be substituted or unsubstituted as for example, with such substituents as those described in relation to substituted phenyl or substituted naphthyl.

The term "$C_7$–$C_{16}$ phenylalkyl" or "$C_7$–$C_{16}$ aralkyl" denotes a $C_1$–$C_{10}$ alkyl group substituted at any position by a phenyl ring. Examples of such a group include benzyl, 2-phenylethyl, 3-phenyl(n-prop-1-yl), 4-phenyl(hex-1-yl), 3-phenyl(n-am-2-yl), 3-phenyl(sec-butyl), and the like. A preferred $C_7$–$C_{16}$ phenylalkyl group is the benzyl group.

The term "$C_7$–$C_{16}$ substituted phenylalkyl" denotes an above $C_7$–$C_{16}$ phenylalkyl group substituted on the $C_1$–$C_{10}$ alkyl portion with one or more, and preferably one or two, groups selected from the group consisting of a halogen, hydroxy, protected hydroxy, keto, $C_2$–$C_3$ cyclic ketal phenyl, amino, protected amino, $C_1$–$C_7$ acyloxy, nitro, carboxy, protected carboxy, carbamoyl, carbamoyloxy, cyano, N-(methyl-sulfonylamino) or $C_1$–$C_4$ alkoxy group, whose phenyl group portion can be substituted with 1 or 2 groups selected from the group consisting of a halogen, hydroxy, protected hydroxy, nitro, $C_1$–$C_{10}$ alkyl, $C_1$–$C_6$ substituted alkyl, $C_1$–$C_4$ alkoxy, carboxy, protected carboxy, carboxymethyl, protected carboxymethyl, hydroxymethyl, protected hydroxymethyl, aminomethyl, protected aminomethyl, amino, (monosubstituted) amino, (disubstituted) amino, a N-(methylsulfonylamino) group, or a phenyl group that is itself substituted or unsubstituted. When either the $C_1$–$C_{10}$ alkyl portion or the phenyl portion or both are mono- or di-substituted, the substituents can be the same or different.

Examples of "$C_7$–$C_{16}$ substituted phenylalkyl" include groups such as 2-phenyl-1-chloroethyl, 2-(4-methoxyphenyl)eth-1-yl, 2,6-dihydroxy-4-phenyl(n-hex-2-yl), 5-cyano-3-methoxy-2-phenyl(n-pent-3-yl), 3-(2,6-dimethylphenyl)n-prop-1-yl, 4-chloro-3-aminobenzyl, 6-(4-methoxyphenyl)-3-carboxy(n-hex-1-yl), 5-(4-aminomethyl-phenyl)-3-(aminomethyl)(n-pent-2-yl), 5-phenyl-3-keto-(n-pent-1-yl), 4-(4-aminophenyl)-4-(I.4-oxetanyl)(n-but-1-yl), and the like.

The term "$C_7$–$C_{16}$ phenylalkenyl" denotes a $C_1$–$C_{10}$ alkenyl group substituted at any position by a phenyl ring. The term "$C_7$–$C_{16}$ substituted phenylalkenyl" denotes a $C_7$–$C_{16}$ arylalkenyl group substituted on the $C_1$–$C_{10}$ alkenyl portion. Substituents can the same as those as defined above in relation to $C_7$–$C_{16}$ phenylalkyl and $C_7$–$C_{16}$ substituted phenylalkyl. A preferred $C_7$–$C_{16}$ substituted phenylalkenyl is 3-(4-nitrophenyl)-2-propenyl.

The term "substituted phenyl" specifies a phenyl group substituted at one or more positions, preferably at one or two positions, with moieties selected from the group consisting of halogen, hydroxy, protected hydroxy, cyano, nitro, $C_1$–$C_{10}$ alkyl, $C_1$–$C_{10}$ substituted alkyl, $C_1$–$C_4$ alkoxy, carboxy, protected carboxy, carboxymethyl, protected carboxymethyl, hydroxymethyl, protected hydroxymethyl, amino, protected anilino, (monosubstituted)amino, protected (monosubstituted) amino, (disubstituted)amino, trifluoromethyl, N-(methylsulfonylamino), or phenyl that is itself substituted or unsubstituted such that, for example, a biphenyl group results.

Illustrative substituents embraced by the term "substituted phenyll" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or di(hydroxy)phenyl groups such as 4-hydroxyphenyl, 3-hydroxyphenyl, 2,4-dihydroxyphenyl, the protected hydroxy derivatives thereof and the like; a nitrophenyl group such as 3- or 4-nitrophenyl, a cyanophenyl group for example, 4-cyanophenyl; a mono- or di(lower alkyl)phenyl group such as 4-methylphenyl, 2,4-dimethylphenyl, 2-methylphenyl, 4-(isopropyl)phenyl, 4-ethylphenyl, 3-(n-prop-1-yl)phenyl and the like: a mono or di(alkoxyl)phenyl group for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl, 3-(4-methylphenoxy)phenyl, and the like; 3- or 4-trifluoromethylphenyl; a mono- or dicarboxyphenyl or (protected carboxy)phenyl group such as 4-carboxyphenyl or 2,4-di(protected carboxy)phenyl; a mono-or di(hydroxymethyl)phenyl or (protected hydroxymethyl) phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl) phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different. For example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like are contemplated.

The term "substituted naphthyl" specifies a naphthyl group substituted with one or more, and preferably one or two moieties selected from the group consisting of a halogen, hydroxy, protected hydroxy, cyano, nitro, $C_1$–$C_{10}$ alkyl, $C_1$–$C_4$ alkoxy, carboxy, protected carboxy, carboxymethyl, protected carboxymethyl, hydroxymethyl, protected hydroxymethyl, amino, protected amino, (monosubstituted) amino, protected (monosubstituted) amino, (disubstituted) amino trifluoromethyl, or a N-(methylsulfonylamino) group. Examples of substituted naphthyl include 2-(methoxy)naphthyl and 4-(methoxy) naphthyl.

The term "substituted indolyl" specifies a indolyl group substituted, either at the nitrogen or carbon, or both, with one or more, and preferably one or two, moieties selected from the group consisting of a halogen, hydroxy, protected hydroxy, cyano, nitro, $C_1$–$C_{10}$ alkyl, $C_1$–$C_{10}$ substituted alkyl, $C_1$–$C_{10}$ alkenyl, $C_7$–$C_{16}$ phenylalkyl, $C_7$–$C_{16}$ substituted phenylalkyl, $C_1$–$C_6$ alkoxy, carboxy, protected carboxy, carboxymethyl, protected carboxymethyl, hydroxymethyl, protected hydroxymethyl, amino, protected amino, monosubstituted amino, or a disubstituted amino group.

Examples of the term "substituted indolyl" includes such groups as 6-fluoro, 5-fluoro, 5-bromo, 5-hydroxy, 5-methyl, 6-methyl, 7-methyl, 1-methyl, 1-ethyl, 1-benzyl, 1-napthylmethyl, and the like. An example of a disubstituted indolyl is 1-methyl-5-methyl indolyl.

The terms "halo" and "halogen" refer to the fluoro, chloro, bromo, or iodo groups.

The term "(monosubstituted)amino" refers to an amino group with one substituent selected from the group consisting of phenyl, substituted phenyl, $C_1$–$C_{10}$ alkyl, and $C_7$–$C_{16}$ arylalkyl, wherein the latter three substituent terms are as defined above. The (monosubstituted)amino can additionally have an amino-protecting group as encompassed by the term "protected (monosubstituted)amino."

The term "(disubstituted)amino" refers to amino groups with two substituents selected from the group consisting of phenyl, substituted phenyl, $C_1$–$C_{10}$ alkyl, and $C_7$–$C_{16}$ arylalkyl wherein the latter three substituent terms are as described above. The two substituents can be the same or different.

The terms "(monosubstituted)guanidino", "(disubstituted)guanidino." and "(trisubstituted)-guanidino" are used to mean that a guanidino group is substituted with one, two, or three substituents, respectively. The substituents can be any of those as defined above in relation to (monosubstituted)-amino and (disubstituted)amino and, where more than one substituent is present, the substituents can be the same or different.

The terms "(monosubstituted) imidizol-one imidazole, "(disubstituted) imidizol-one imidazole." and "(trisubstituted) imidizol-one imidazole" mean compounds in which the imidizol-one imidazole group is substituted with one, two, or three substituents, respectively. The substituents can be any of those as defined above in relation to a (monosubstituted)-amino or (disubstituted)amino group and where more than one substituent is present. The substituents can be the same or different.

The term "amino-protecting group" as used herein refers to one or more selectively removable substituents on the amino group commonly employed to block or protect the amino functionality. The term "protected (monosubstituted) amino" means there is an amino-protecting group on the monosubstituted amino nitrogen atom. In addition, the term "protected carboxamide" means there is an amino-protecting group present replacing the proton of the amido nitrogen so that di-N-alkylation.

Examples of such amino-protecting groups include the formyl ("For") group, the trityl group (Trt), the phthalimido group, the trichloroacetyl group, the chloroacetyl, bromoacetyl, and iodoacetyl groups. Urethane blocking groups, such as t-butoxy-carbonyl ("Boc"), 2-(4-biphenylyl)propyl(2)-oxycarbonyl ("Bpoc"), 2-phenylpropyl(2) oxycarbonyl ("Poc"), 2-(4-xenyl)-isopropoxycarbonyl, 1,1-diphenylethyl(1)oxycarbonyl, 1,1-diphenylpropyl(1) oxycarbonyl, 2-(3,5-dimethoxyphenyl) propyl(2) oxycarbonyl ("Ddz"), 2-(p-5-toluyl)propyl-(2) oxycarbonyl, cyclo-pentanyloxycarbonyl, 1-methylcyclopentanyl-oxycarbonyl, cyclohexanyloxycarbonyl, 1-methyl-cyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluoroenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benz-isoxalylmethoxycarbonyl, 4-acetoxybenzyloxycarbonyl, 2,2,2-trichloroethoxycarbonyl, 2-ethynyl(2)propoxycarbonyl, cyclopropylmethoxycarbonyl, isobornyloxycarbonyl, 1-piperidyloxycarbonyl, benzyloxycarbonyl ("Z"), 4-phenylbenzyloxycarbonyl, 2-methylbenzyloxycarbonyl, α-2,4,5,-tetramethylbenzyloxycarbonyl ("Tmz"), 4-methoxybenzyl-oxycarbonyl, 4-fluorobenzyloxycarbonyl, 4-chloro-benzyloxycarbonyl, 3-chlorobenzyloxycarbonyl, 2-chlorobenzyloxycarbonyl, dichlorobenzyloxycarbonyl, 4-bromobenzyloxycarbonyl, 3-bromobenzyloxycarbonyl, 4-nitrobenzyloxycarbonyl, 4-cyanobenzyIioxycarbonyl, 4-(decyloxy)benzyloxycarbonyl, and the like, the benzoyl-methylsulfonyl group, dithiasuccinoyl ("Dts') group, the 2-(nitro)phenylsulfenyl group ("Nps'), the diphenylphosphine oxide group, and like amino-protecting groups. The species of amino-protecting group employed is usually not critical so long as the derivatized amino group is stable to the conditions of the subsequent reactions and can be removed at the appropriate point without disrupting the remainder of the compound. Preferred amino-protecting groups are Boc and Fmoc.

Further examples of amino-protecting groups embraced to by the above term are well known in organic synthesis and the peptide art and are described by, for example T. W. Greene and P. G. M. Wuts, *Protective Groups in Organic Synthesis*, $2^{nd}$ ed., John Wiley and Sons. New York., Chapter 7, 1991; M. Bodanzsky, *Principles of Peptide Synthesis*, $1^{st}$ and $2^{nd}$ revised eds., Springer-Verlag, New York, 1984 and 1993; and Stewart and Young, *Solid Phase Peptide Synthesis*, $2^{nd}$ ed., Pierce Chemical Co, Rockford. IL 1984.

The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-methoxytrityl, 4,4',4"-trimethoxytrityl, 2-phenylprop-2-yl, trimethylsilyl, t-butyldimethylsilyl, 2,2,2-trichloroethyl, β-(trimethylsilyl)ethyl, β-[di(n-butyl)methylsilyl]ethyl, p-toluenesulfonylethyl, 4-nitrobenzyl-sulfonylethyl, allyl, cinnamyl, 1-(trimethylsilylmethyl)-prop-1-en-3-yl, and like moieties. The species of carboxy-protecting group employed is also usually not critical so long as the derivatized carboxylic acid is stable to the conditions of subsequent reactions and can be removed at the appropriate point without disrupting the remainder of the molecule.

Further examples of these groups are found in E. Haslam, *Protective Groups in Organic Chemistry*, J. G. W. McOmie Ed., Plenum Press, New York 1973, Chapter 5 and T. W. Greene and P. G. M. Wuts, *Protective Groups in Organic Synthesis* $2^{nd}$ ed., John Wiley and Sons, New York, 1991, Chapter 5, each of which is incorporated herein by reference. A related term is "protected-carboxy", which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl and 2,2,2-trichloroethoxycarbonyl groups, and the like. The species of hydroxy-protecting groups is also usually not critical so long as the derivatized hydroxyl group is stable to the conditions of subsequent reaction(s) and can be removed at the appropriate point without disrupting the remainder of the compound.

Further examples of hydroxy-protecting groups are described by C. B. Reese and E Haslam, *Protective Groups in Organic Chemistry*, J. G. W. McOmie, Ed., Plentun Press, New York 1973, Chapters 3 and 4, respectively, and T. W. Greene and P. G. M. Wuts, *Protective Groups in Organic Synthesis*, $2^{nd}$ ed., John Wiley and Sons, New York, 1991, Chapters 2 and 3, whose disclosures are also incorporated by reference.

The substituent term "$C_1$–$C_4$ alkylthio" refers to sulfide groups such as methylthio, ethylthio, n-propylthio, isopropylthio, α-butylthio, t-butylthio and like groups.

The substituent term "$C_1$–$C_4$ alkylsulfoxide" indicates sulfoxide groups such as methylsulfoxide, ethylsulfoxide, α-propylsulfoxide, iso-propyl-sulfoxide, n-butylsulfoxide, sec-butylsulfoxide, and the like.

The term "$C_1$–$C_4$ alkylsulfonyl" encompasses groups such as methylsulfonyl, ethylsulfonyl, n-propylsulfonyl, isopropylsulfonyl, a-butylsulfonyl, t-butylsulfonyl, and the like.

Phenylthio, phenyl sulfoxide, and phenylsulfonyl compounds are known in the art and these have their art-recognized definitions. By "substituted phenylthio", "substituted phenyl sulfoxide", and "substituted phenylsulfonyl", is meant that the phenyl can be substituted as described above in relation to "substituted phenyl."

The substituent terms "cyclic $C_2$–$C_{10}$ alkylene", "substituted cyclic $C_2$–$C_{10}$ alkylene", "cyclic $C_2$–$C_{10}$ heteroalkylene." and "substituted cyclic $C_2$–$C_{10}$ heteroakylene" defines a cyclic group bonded ("fused") to the phenyl radical. The cyclic group can be saturated or contain one or two double bonds. Furthermore, the cyclic group can have one or two methylene groups replaced by one or two oxygen, nitrogen or sulfur atoms.

The cyclic alkylene or heteroalkylene group can be substituted once or twice by substituents selected from the group consisting of hydroxy, protected-hydroxy, carboxy, protected-carboxy, keto, ketal, $C_1$–$C_4$ alkoxycarbonyl, $C_1$–$C_4$ alkanoyl, $C_1$–$C_{10}$ alkyl, carbamoyl, $C_1$–$C_4$ alkoxy, $C_1$–$C_4$, alkylthio, $C_1$–$C_4$ alkylsulfoxide, $C_1$–$C_4$ alkylsulfonyl, halo, amino, protected-amino, hydroxymethyl and a protected-hydroxymethyl group.

A cyclic alkylene or heteroalkylene group fused onto the benzene radical can contain two to ten ring members, but it preferably contains four to six members. Examples of such saturated cyclic groups include a bicyclic ring system that is a 2,3-dihydroindanyl or a tetralin ring. When the cyclic groups are unsaturated, examples occur when the resultant bicyclic ring system is a naphthyl ring or indanyl.

An example of a cyclic group that can be fused to a phenyl radical that has two oxygen atoms and that is fully saturated is dioxanyl. Examples of fused cyclic groups that each contain one oxygen atom and one or two double bonds occur when the phenyl ring is fused to a furyl, pyranyl, dihydrofuryl or dihydropyranyl ring. Cyclic groups that each have one nitrogen atom and contain one or two double more double bonds are illustrated where the phenyl is fused to a pyridino or pyrano ring. An example of a fused ring system having one nitrogen and two phenyl radicals is a carbozyl group. Examples of cyclic groups that each have one sulfur atom and contain one or two double bonds occur where the benzene ring is fused to a thieno, thiopyrano, dihydrothieno, or dihydrothiopyrano ring. Examples of cyclic groups that contain two heteroatoms selected from sulfur and nitrogen and one or two double bonds occur where the phenyl ring is fused to a thiazolo, isothiazolo, dihydrothiazolo or dihydroisothiazolo ring. Examples of cyclic groups that contain two heteroatoms selected from oxygen and nitrogen and one or two double bonds occur where the benzene ring is fused to an oxazole, isoxazole, dihydroxazole or dihydroisoxazole ring. Examples of cyclic groups that contain two nitrogen heteroatoms and one or two double bonds occur where the benzene ring is fused to a pyrazolo, imidazolo, dihydropyrazolo or dihydroimidazolo ring.

Examples of cyclic groups that each have one nitrogen atom and contain one or two double more double bonds occur when the phenyl is fused to a pyridino or pyrano ring. An example of a fused ring system having one nitrogen and two phenyl radicals is a carbozyl group. Examples of cyclic groups that each have one sulfur atom and contain one or two double bonds occur when the phenyl is fused to a thieno, thiopyrano, dihydrothieno, or dihydrothiopyrano ring.

Examples of cyclic groups that contain two heteroatoms selected from sulfur and nitrogen and one or two double bonds occur when the phenyl ring is fused to a thiazolo, isothiazolo, dihydrothiazolo or dihydroisothiazolo ring. Examples of cyclic groups that contain two heteroatoms selected from oxygen and nitrogen and one or two double bonds occur when the benzene ring, is fused to an oxazolo, isoxazolo, dihydroox-azolo or dihydroisoxazolo ring. Examples of cyclic groups which contain two nitrogen heteroatoms and one or two double bonds occur when the benzene ring is fused to a pyrazolo, Imidazolo, dihydropyrazolo or dihydroimidazolo ring.

Pharmaceutical Compositions

A pharmaceutical composition for treating infections, pain, or other indications treatable by a contemplated imidazo-imidazol-one is administered to a subject in need of the medication at dosage levels of about 0.7 to about 7000 mg per day, and preferably about 1 to about 500 mg per day, for a normal human adult of approximately 70 kg of body weight. This broadly translates into a dosage of about 0.01 to about 100 mg/kg of body weight per day of an imidizo-imidazol-one compound of Formula I as active ingredient. The specific dosages employed, however, can be varied depending upon the requirements of the patient, the severity of the condition being treated, and the activity of the compound being employed. The determination of optimum dosages for a particular situation is within the skill of the art.

One or more of the imidizo-imidazol-one compounds of Formula I can be present as a pharmaceutically-acceptable salt. The term "pharmaceutically-acceptable salt" encompasses those salts that form with the carboxylate anions or ammonium cations and include salts formed with the organic and inorganic cations and anions discussed below. Furthermore, the term includes salts that form by standard acid-base reactions with basic groups (such as amino groups) and organic or inorganic acids. Such acids include hydrochloric, sulfuric, phosphoric, acetic, succinic, citric lactic, maleic, fumaric, palmitic, cholic, pamoic, mucic, D-glutamic, d-camphoric, glutaric, phthalic, tartaric, lauricc, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium and calcium): ammonium; and the organic cations such as (dibenzylammonium, benzylammonium, 2-hydroxymethylammonium, bis(2-hydroxyethyl) ammonium, phenylethylbenzyl ammonium, dibebenzylethylenediammoniurn, and like cations). Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. A preferred cation for the carboxylate anion is the sodium cation.

A compound of Formula I can also be present as a solvate and hydrate. Thus, these compounds can crystallize with, for example, waters of hydration, or one, a number of, or any fraction thereof of molecules of the mother liquor solvent. The solvates and hydrates of such compounds are included within the scope of this invention.

One or more of the contemplated compounds can be in the biologically active ester form, such as the non-toxic, metabolically-labile ester-form. Such ester forms induce increased blood levels and prolong the efficacy of the corresponding non-esterified forms of the compounds. Ester groups that can be used include the lower alkoxymethyl groups ($C_1$–$C_4$ alkoxymethyl) for example, methoxymethyl, ethoxymethyl, isopropoxymethyl and the like; the —($C_1$–$C_4$) alkoxyethyl groups, for example methoxyethyl, ethoxyethyl, propxyethyl, iso-propoxyethyl, and the like, the 2-oxo-1,3-dioxolen-4-ylmethyl groups such as 5-methyl-2-oxo-1,3-dioxolen-4-ylmethyl, 5-phenyl-2-oxo-1,3-dioxolen-4-ylmethyl, and the like, the $C_1$–$C_3$ alkylthiomethyl groups, for example methylthiomethyl, ethylthiomethyl, isopropylthiomethyl, and the like, the acyloxymethyl groups, for example pivaloyloxymethyl, pivaloyloxyethyl, a-acetoxymethyl, and the like, the ethoxycarbonyl-1-methyl group, the a-acetoxyethyl, the 3-phthalidyl or 5,6-dimethylphtalidyl groups, the 1-($C_1$–$C_4$ alkyloxycarbonyloxy)ethyl groups such as the 1-(ethoxycarbonyloxy)ethyl group, and the 1-($C_1$–$C_4$ alkylaminocarbonyloxy)ethyl groups such as the 1-methylaminocarbonyloxyethyl group.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

A pharmaceutical composition can include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active urea. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

Library Synthesis and Use

As used herein, a chemical or combinatorial " library" is an intentionally created collection of a plurality of structurally similar, but different molecules. By "structurally similar", it is meant that the constituent compounds of a library have the same ring structure; i.e., a bicyclic imidizo-imidazol-one ring, and at least two positions at which substituents are bonded to the ring structure. It is preferred that the member compounds of the library also have the same substitution pattern of substituent groups; i.e., that the at least two substituents be bonded to the same ring positions in each member compound. The molecule members of the library are different in that each member has at least one different substituent group from the other members of the library. A library can contain two to thousands or millions of member compounds.

A particular library can also be comprised of members whose substituent groups are all different from each other. Thus, where the shared ring structure contains substituent groups at a plurality of positions, a library can be prepared in which the member molecules contain different groups at each position.

Alternatively, a plurality of sub-libraries or sets can also be prepared in which a first set has a first substituent that is held constant for all of the members (is present in all members) of the set, whereas the groups at the other substituent positions are different and constitute a mixture of groups at each substituent position. A second set of that plurality has a second, different, first substituent, and the same mixture of different groups at the other substituent positions. A third set of that plurality has a third, different first substituent, and the same mixture of different groups at the other substituent positions, and so on until one decides to stop making sets with different first substituents. Such set pluralities of structurally similar, but different compounds are also often referred to as libraries of libraries, and are particularly useful in ascertaining which compound or compounds of a library are active in an assay of choice.

A library can be prepared by the synthetic means discussed below or otherwise herein and screened for biological activity in a variety of formats (e.g. libraries of soluble molecules). Libraries of compounds can be attached to resin beads, silica chips or other solid supports). The libraries can be screened in any variety of assays, such as those detailed below as well as others useful for assessing the biological activity of imidazo-imidazol-ones. The libraries typically contain at least one active compound and are generally prepared such that the compounds are in equimolar quantities.

The nonsupport-bound library mixtures prepared herein were screened in solution in radio-receptor inhibition assays described in detail hereinafter. Deconvolution of highly active mixtures can then be carried out by iterative, or positional scanning methods. These techniques, the iterative approach or the positional scanning approach, can be utilized for finding other active compounds within the libraries of the present invention using any one of the below-described assays or others well known in the art.

The iterative approach is well-known and is set forth in general in Houghten et al., *Nature*, 354, 84–86 (1991) and Dooley et al., *Science*, 266, 2019–2022 (1994), both of which are incorporated herein by reference. In the iterative approach, for example, sub-libraries of a molecule having three variable groups are made wherein the first variable substituent is defined (known and held constant) within the sub-library. Each of the compounds with the defined variable group is reacted separately with each of the other possibilities at the second variable group position and the third variable position is a mixture of all of the possible substituents to form a plurality of sub-libraries whose first two substituent groups are known. These sub-libraries are each assayed to define the identity of the second variable in the sub-library having the highest activity in the screen of choice.

A new sub-library with the first two variable positions defined is separately reacted with each of the other possibilities at the remaining undefined variable position. As before, the identity of the third variable position in the sub-library having the highest activity is determined.

If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various libraries as described, for example, in R. Houghten et al. PCT/US91/08694 and U.S. Pat. No. 5,556,762, both of which are incorporated herein by reference. The positional scanning approach is used as described below in the preparation and screening of the libraries.

In the positional scanning approach, sub-libraries are made defining only one variable substituent with each set of sub-libraries and all possible sub-libraries with each single variable substituent defined (and all other possibilities at all of the other variable positions) is made and tested. From the instant description one skilled in the art can synthesize libraries wherein two fixed substituent positions are defined at a time. From the assaying of each single-variable defined library, the optimum substituent at that position is determined, pointing to the optimum or at least a series of compounds having a maximum of the desired biological activity. Thus, the number of sub-libraries for compounds with a single substituent position defined is the number of different substituents desired at that position, and the number of all the compounds in each sub-library is the product of the number of substituents at each of the other variables.

The [3,5,7]-1H-imidazo[1,5-a]imidazol-2(3H)-one libraries and compounds of Formula I can be prepared according to the general reaction Scheme 1, which for ease of description is shown using single amino acids. The reaction scheme shown forms a single compound or enantiomeric pair of compounds of Formula I. Where libraries are desired, a mixture of amino acids (Boc-$R^1$aa-OH or Boc-$R^2$aa-OH), or carboxylic acids ($R^3$—$CO_2H$) is used for at least one of the coupling steps.

The individual compounds and libraries are prepared using solid-phase techniques. The solid-phase resin, here, p-methylbenzhydrylamine resin (p-MBHA), is indicated in Scheme 1 by the large circle and dash.

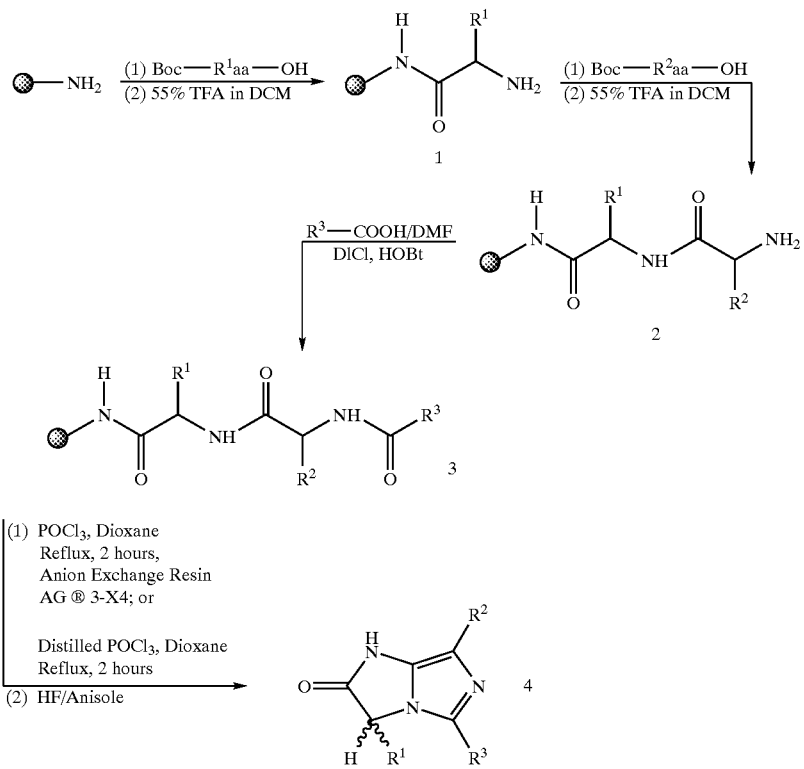

Scheme 1

Starting from p-methylbenzhydrylamine (MBHA) resin-bound N-tert-butyloxycarbonyl (Boc) amino acid 1 (Boc-$R^1$aa-OH), the Boc group was removed using a mixture of trifluoroacetic acid (TFA) and dichloromethane (DCM). The resulting amine salt was neutralized, and the resulting primary amine was N-acylated with a second Boc-protected amino acid (Boc-$R^2$aa-OH) as before, to provide the resin bound-monopeptide 2.

Following removal of the Boc protecting group using 55% of trifluoroacetic acid in dichloromethane, the resulting free amine was acylated with a carboxylic acid 3 ($R^3$—$CO_2H$) in dimethylformamide (DMF) using diisopropylcarbodiimide (DICI) and hydroxybenzotriazole (HOBt) to effect coupling. The bicyclic [3,5,7]-1H-imidazo[1,5-a]-imidazol-2(3H)-one 4 was obtained via cyclization using the conditions of Bischler-Napieralski, with 25-fold excess of phosphorus oxychloride ($POCl_3$) in refluxing 1,4-dioxane in the presence of a 30-fold excess of anion exchange resin (AG® 3-X4) [Bischler, A.; Napieralski, B. *Chem. Ber., (1893)*, 26, 1903; W. M. Whaley, T. R. Govindachari, *Org. React.*, 6, 74 (1951); T. Kametani et al., *Tetrahedron*, 27, 5367 (1971); G. Fodor et al., *Angew. Chem. Int. Ed.*, 11, 919 (1972); G. Fodor, S. Nagubandi, *Tetrahedron*, 36, 1279 (1980); idem, *Heterocycles*, 15, 165 (1981)]. More recent syntheses using freshly distilled $POCl_3$ in the absence of the anion exchange resin have provided yields in the range of about 80 percent. The desired products were readily obtained following cleavage from the resin with anhydrous HF in anisole to provide compound 4.

Following the strategy described in Scheme 1, with the parallel synthesis approach, commonly referred to as the "tea-bag" method [Houghten et al., Nature, 354: 84–86 (1991)], libraries are synthesized with 33 different amino acids to provide the R group at $R^1$, 33 different amino acids to provide the R group at $R^2$, and 92 different carboxylic acids to provide the R group at $R^3$, in which the individual building blocks were varied, while fixing the remaining two positions.

Any variety of amino acids can be used with the present invention as described above to prepare a vast array of bicyclic [3,5,7]-1H-imidazo[1,5-a]-imidazol-2(3H)-one with different $R^1$, $R^2$ and $R^3$ groups. As described above, thirty-three first amino acids were coupled to the resin, which amino acids provide the $R^1$ substituent group. The thirty-three amino acids included Ala, Phe, Gly, His(DNP), Ile, Lys(CBZ), Leu, Met, Arg(Tos), Nva, Ser(Bzl), Thr(Bzl), Val, Tyr(CHO), Tyr(BrZ), Nle, Cha, ala, phe, his(DNP), ile, lys(CBZ), leu, met, arg(Tos), ser(Bzl), thr(Bzl), val, trp (CHO), tyr(BrZ), nle, nva, cha.

After the above-described 33 reactions and removal of the BOC protecting group, a single amino acid (valine) was coupled as the second amino acid, thereby providing the $R^2$ group. After removal of the second BOC group, a single carboxylic acid, acetic acid, was coupled to provide the $R^3$ group for the 33 different compounds. Those compounds were thereafter cyclized to form compounds of Formula I and cleaved from the resin.

Another set or sub-library of 33 compounds was prepared by reacting a single amino acid (valine) with the resin to provide one $R^1$ group. After removal of the BOC protecting group, each of the above 33 amino acids was then separately coupled to provide 33 resin-linked peptides with the same $R^1$ group and one of the 33 different $R^2$ groups. On removing the second BOC group, a single carboxylic acid (acetic acid) was bonded to the free amino group to provide a single $R^3$ group for the resin-linked peptides. Theses compounds were also cyclized to form compounds of Formula I, and cleaved from the resin.

In a third set or sub-library preparation, a single amino acid (valine) was coupled to the resin to provide a single $R^1$ group, the BOC group was removed and a second amino acid (valine) was coupled to provide a single $R^2$ group and form a dipeptide. After removal of the second BOC group, the dipeptide was separately reacted with each of the 92 carboxylic acids listed in Table 2, below, to provide 92 different $R^3$ groups. The acylated peptides were thereafter cyclized, cleaved from the solid support resin and recovered. Assays using those compounds are discussed hereinafter.

As used herein, abbreviations for the various amino acid side-chain protecting groups are as follows: "Trt" for trityl, "tBu' for tert-butyl, "Boc" or "BOC" for tert-butoxycarbonyl, "Tos" for toluenesulfonyl or tosyl, "DNP" for dinitrophenyl, "Bzl" for benzyl, "CHO" for formyl, "Brz" for 2-bromobenzyloxycarbonyl and "CBZ" for carbobenzoxy. As can be seen from the side chains exemplified in the table below, it should be appreciated from the above-described embodiments of $R^1$ and $R^2$ are merely illustrative of the R groups that can be present. Following usual notation, L-amino acids are referred to with an initial capital letter as in Val, whereas D-amino acids are referred to with an initial lower case letter as in ala.

TABLE 1

| Amino acid name | | Side chain R |
|---|---|---|
| Full | 3-letter code | (For $R^1$ and $R^2$) |
| Glycine | Gly | ⁓H |
| Alanine | Ala | ⁓$CH_3$ |
| Valine | Val | ⁓$CH(CH_3)_2$ |
| Leucine | Leu | ⁓$CH_2$—$CH(CH_3)_2$ |
| Isoleucine | Ile | ⁓$CH(CH_3)CH_2CH_3$ |
| Lysine | Lys | ⁓$(CH_2)_4$—$NH_2$ |
| Serine | Ser | ⁓$CH_2$—OH |
| Threonine | Thr | ⁓$CH(CH_3)$—OH |
| Phenylalanine | Phe | ⁓$CH_2$—⌬ |
| Tyrosine | Tyr | ⁓$CH_2$—⌬—OH |
| Norvaline | Nva | ⁓$(CH_2)_2$—$CH_3$ |
| Norleucine | Nle | ⁓$(CH_2)_3$—$CH_3$ |
| Naphthylalanine | Nal | ⁓$CH_2$—(naphthyl) |
| Cyclohexylalanine | Cha | ⁓$CH_2$—(cyclohexyl) |
| Methionine | Met | ⁓$CH_2$—$CH_2$—S—$CH_3$ |

TABLE 1-continued

| Amino acid name | | Side chain R |
|---|---|---|
| Full | 3-letter code | (For $R^1$ and $R^2$) |
| Phenylglycine | Phg | 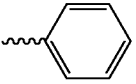 |

A variety of carboxylic acids can also be used in the acylation step of the reaction of Scheme 1, thereby providing a wide array of substituents at the $R^3$ position of the bicyclic [3,5,7]-1H-imidazo[1,5-a]imidazol-2(3H)-one. Ninety-two carboxylic acids were used in preparing the [3,5,7]-1H-imidazo[1,5-a]imidazol-2(3H)-one libraries. The ninety-two $R^3$ groups were provided by the following carboxylic acids:

TABLE 2

Exemplary Carboxylic Acids

1-Phenyl-1-Cyclopropanecarboxylic Acid
2-Phenylbutyric Acid
3-Phenylbutyric Acid
m-Tolylacetic Acid
3-Fluorophenylacetic Acid
3-Bromophenylacetic Acid
α,α,α-Trifluoro-m-tolyl-acetic Acid
p-Tolylacetic Acid
4-Fluorophenylacetic Acid
3-Methoxyphenylacetic Acid
4-Bromophenylacetic Acid
4-Methoxyphenylacetic Acid
4-Ethoxyphenylacetic Acid
4-Isobutyl-α-methylphenylacetic Acid
3,4-Dichlorophenylacetic Acid
3,5-Bis(Trifluoromethyl)phenylacetic Acid
3-(3,4-Dimethoxyphenyl)propionic Acid
4-Biphenylacetic Acid
α-Methylcinnamic Acid
2-(Trifluoromethyl)cinnamic Acid
(3,4-Dimethoxyphenyl)acetic Acid
3,4-(Methylenedioxy)phenylacetic Acid
2-Methoxycinnamic Acid
3,4-(Methylenedioxy)cinnamic Acid
2-Hydroxycinnamic Acid
Benzoic Acid
4-Chlorocinnamic Acid
m-Anisic Acid
4-Isopropylbenzoic Acid
4-Vinylbenzoic Acid
4-Fluorobenzoic Acid
4-Bromobenzoic Acid
3,4-Dimethoxycinnamic Acid
4-Hydroxybenzoic Acid
trans-Cinnamic Acid
3,4-Dimethylbenzoic Acid
3-Fluoro-4-methylbenzoic Acid
3-Bromo-4-methylbenzoic Acid
3-Iodo-4-methylbenzoic Acid
3,4-Dichlorobenzoic Acid
4-Biphenylcarboxylic Acid
3,4-Difluorobenzoic Acid
m-Toluic Acid
Phenylacetic Acid
Hydrocinnamic Acid
3-Methoxy-4-methylbenzoic Acid
4-Phenylbutyric Acid
4-Butylbenzoic Acid
3,5-Dimethylbenzoic Acid
3,5-Bis(Trifluoromethyl)benzoic Acid
3,4-Dimethoxybenzoic Acid
4-Ethyl-4-biphenylcarboxylic Acid
3,4,5-Trimethoxybenzoic Acid
3,4,5-Triethoxybenzoic Acid TABLE 2-continued Exemplary Carboxylic Acids Butyric Acid
Heptanoic Acid
Isobutyric Acid
(+/−)-2-Methylbutyric Acid
Isovaleric Acid
3-Methylvaleric Acid
4-Methylvaleric Acid
(+/−)-2-Ethylhexanoic Acid
Crotonic Acid
Vinylacetic Acid
trans-3-Hexenoic Acid
2-Ethyl-2-Hexenoic Acid
p-Toluic Acid
p-Anisic Acid
Trimethylacetic Acid
tert-Butylacetic Acid
Cyclohexanecarboxylic Acid
Cyclohexylacetic Acid
Dicyclohexylacetic Acid
Cyclohexanebutyric Acid
Cycloheptanecarboxylic Acid
Acetic Acid
2-Methylcyclopropanecarboxylic Acid
Cyclobutanecarboxylic Acid
Cyclopentanecarboxylic Acid
3-Cyclopentylpropionic Acid
2-Furoic Acid
Cyclohexanepropionic Acid
4-Methyl-1-Cyclohexanecarboxylic Acid
4-tert-Butyl-Cyclohexanecarboxylic Acid
1-Adamantanecarboxylic Acid
4-Methylcyclohexaneacetic Acid
2,4-Hexadienoic Acid
Tiglic Acid
2-Norbornaneacetic Acid
1-Adamantaneacetic Acid
2-Ethylbutyric Acid
2-Thiophenecarboxylic Acid

EXAMPLE 1

Individual Syntheses of [3,5,7]-1H-imidazo[1,5-a]-imidazol-2 (3H)-ones

The compounds listed below were prepared following the synthetic route illustrated and discussed in regard to Scheme 1, above. A total of 158 individual compound syntheses or pools were carried out, with 73 of those reactions yielding either no product, starting material or other than the expected product. The reason for the apparent failures is not completely understood, but is believed to be due to steric hindrance. Recent syntheses with about twenty compounds indicated yields of product in each synthesis when freshly distilled $POCl_3$ was used in the synthesis. The reagent used for the preparation of each of the three "R" groups; i.e., the amino acid or carboxylic acid, is listed in the three columns labeled $R^1$, $R^2$ and $R^3$, respectively. Mass spectral data from the syntheses are shown in the right hand-most column of the table below.

Structure I

Compound of formula I with substituents R¹, R², R³ on the imidazolone/imidazole scaffold.

| Pool # | R¹ | R² | R³ (Acid) | MW ] (calc) | M + H (calc) | Single major peak (MW) found |
|---|---|---|---|---|---|---|
| 1 | Gly | Val | Acetic | 179.11 | 180.11 | |
| 2 | Ala | Val | Acetic | 193.12 | 194.12 | 194.1 |
| 3 | Val | Val | Acetic | 221.15 | 222.15 | 222.1 |
| 4 | Leu | Val | Acetic | 235.17 | 236.17 | 236.2 |
| 5 | Ile | Val | Acetic | 235.17 | 236.17 | 236.1 |
| 6 | Ser | Val | Acetic | 209.12 | 210.12 | |
| 7 | Thr | Val | Acetic | 223.13 | 224.13 | |
| 8 | Lys | Val | Acetic | 250.16 | 251.16 | |
| 9 | Arg | Val | Acetic | 278.19 | 279.19 | 279.6 |
| 10 | Met | Val | Acetic | 253.12 | 254.12 | |
| 11 | Nle | Val | Acetic | 235.17 | 236.17 | 236.2 |
| 12 | Nva | Val | Acetic | 221.15 | 222.15 | 222.2 |
| 13 | Cha | Val | Acetic | 275.2 | 276.20 | 276.2 |
| 14 | Phe | Val | Acetic | 269.15 | 270.15 | |
| 15 | Tyr | Val | Acetic | 285.15 | 286.15 | |
| 16 | Trp | Val | Acetic | 387.16 | 388.16 | |
| 17 | His(DNP) | Val | Acetic | 425.14 | 426.14 | 426.2 |
| 18 | ala | Val | Acetic | 193.12 | 194.12 | 194.1 |
| 19 | val | Val | Acetic | 221.15 | 222.15 | 222.2 |
| 20 | leu | Val | Acetic | 235.17 | 236.17 | 236.2 |
| 21 | ile | Val | Acetic | 235.17 | 236.17 | 236.2 |
| 22 | ser | Val | Acetic | 209.12 | 210.12 | |
| 23 | thr | Val | Acetic | 223.13 | 224.13 | |
| 24 | lys | Val | Acetic | 250.16 | 251.16 | |
| 25 | arg | Val | Acetic | 264.17 | 265.17 | |
| 26 | met | Val | Acetic | 253.12 | 254.12 | |
| 27 | nle | Val | Acetic | 235.17 | 236.17 | 236.2 |
| 28 | nva | Val | Acetic | 221.15 | 222.15 | 222.2 |
| 29 | cha | Val | Acetic | 275.2 | 276.20 | 276.2 |
| 30 | phe | Val | Acetic | 269.15 | 270.15 | 270.2 |
| 31 | tyr | Val | Acetic | 285.15 | 286.15 | 286.2 |
| 32 | trp | Val | Acetic | 308.16 | 309.16 | |
| 33 | his(DNP) | Val | Acetic | 425.14 | 426.14 | 462 |
| 34 | Val | Gly | Acetic | 179.11 | 180.11 | 180.1 |
| 35 | Val | Ala | Acetic | 193.12 | 194.12 | 194.1 |
| 36 | Val | Val | Acetic | 221.15 | 222.15 | 222.1 |
| 37 | Val | Leu | Acetic | 235.17 | 236.17 | 236.1 |
| 38 | Val | Ile | Acetic | 235.17 | 236.17 | 236.1 |
| 39 | Val | Ser | Acetic | 209.12 | 210.12 | |
| 40 | Val | Thr | Acetic | 223.13 | 224.13 | |
| 41 | Val | Lys | Acetic | 250.16 | 251.16 | 251.2 |
| 42 | Val | Arg | Acetic | 278.19 | 279.19 | 279.2 |
| 43 | Val | Met | Acetic | 253.12 | 254.12 | |
| 44 | Val | Nle | Acetic | 235.17 | 236.17 | 236.1 |
| 45 | Val | Nva | Acetic | 221.15 | 222.15 | 222.1 |
| 46 | Val | Cha | Acetic | 275.2 | 276.20 | 276.2 |
| 47 | Val | Phe | Acetic | 269.15 | 270.15 | 270.1 |
| 48 | Val | Tyr | Acetic | 285.15 | 286.15 | 286.1 |
| 49 | Val | Trp | Acetic | 387.16 | 388.16 | |
| 50 | Val | His | Acetic | 425.14 | 426.14 | 426.2 |
| 51 | Val | Ala | Acetic | 193.12 | 194.12 | 194.1 |
| 52 | Val | Val | Acetic | 221.15 | 222.15 | 222.1 |
| 53 | Val | Leu | Acetic | 235.17 | 236.17 | 236.1 |
| 54 | Val | Ile | Acetic | 235.17 | 236.17 | 236.2 |
| 55 | Val | Ser | Acetic | 209.12 | 210.12 | |
| 56 | Val | Thr | Acetic | 223.13 | 224.13 | |
| 57 | Val | Lys | Acetic | 250.16 | 251.16 | 251.2 |
| 58 | Val | Arg | Acetic | 278.19 | 279.19 | 279.2 |
| 59 | Val | Met | Acetic | 253.12 | 254.12 | 254.1 |
| 60 | Val | nle | Acetic | 235.17 | 236.17 | 236.1 |
| 61 | Val | nva | Acetic | 221.15 | 222.15 | 222.1 |
| 62 | Val | cha | Acetic | 275.2 | 276.20 | 276.2 |
| 63 | Val | phe | Acetic | 269.15 | 270.15 | 270.1 |
| 64 | Val | tyr | Acetic | 285.15 | 286.15 | 286.1 |
| 65 | Val | trp | Acetic | 308.16 | 309.16 | |
| 66 | Val | his | Acetic | 425.14 | 426.14 | 426.1 |
| 67 | Val | Val | 1-Phenyl-1-cyclopropane-carboxylic | 323.2 | 324.20 | 324.2 |
| 68 | Val | Val | 2-Phenyl-butyric | 325.22 | 326.22 | 326.2 |
| 69 | Val | Val | 3-Phenyl-butyric | 325.22 | 326.22 | 326.2 |
| 70 | Val | Val | m-Tolylacetic | 311.2 | 312.20 | 312.2 |
| 71 | Val | Val | 3-Fluoro-phenylacetic | 315.17 | 316.17 | 316.2 |
| 72 | Val | Val | 3-Bromo-phenylacetic | 375.11 | 376.11 | 376.2 |
| 73 | Val | Val | (α,α,α-Trifluoro-m-Tolyl)acetic | 365.17 | 366.17 | 366.2 |
| 74 | Val | Val | p-Tolylacetic | 311.2 | 312.20 | 312.2 |
| 75 | Val | Val | 4-Fluoro-phenylacetic | 315.17 | 316.17 | 316.1 |
| 76 | Val | Val | 3-Methoxy-phenylacetic | 327.19 | 328.19 | 328.2 |
| 77 | Val | Val | 4-Bromo-phenylacetic | 375.11 | 376.11 | 376.1 |
| 78 | Val | Val | 4-Methoxy-phenylacetic | 327.19 | 328.19 | 328.2 |
| 79 | Val | Val | 4-Ethoxy-phenylacetic | 341.21 | 342.21 | 342.2 |
| 80 | Val | Val | 4-Isobutyl-alpha-methylphenyl-acetic | 367.26 | 368.26 | 368.1 |
| 81 | Val | Val | 3,4-Dichloro-phenylacetic | 365.11 | 366.11 | 366.2 |
| 82 | Val | Val | 3,5-Bis-(Trifluoro-methyl)-phenylacetic | 433.16 | 434.16 | 434.1 |
| 83 | Val | Val | 3-(3,4-Dimethoxy-phenyl)-propionic | 371.22 | 372.22 | 372.2 |
| 84 | Val | Val | 4-Biphenyl-acetic | 373.22 | 374.22 | 374.2 |
| 85 | Val | Val | α-Methyl-cinnamic | 323.2 | 324.20 | 324.2 |
| 86 | Val | Val | 2-(Trifluoro-methyl)cinnamic | 377.17 | 378.17 | 378.2 |
| 87 | Val | Val | (3,4-Dimethoxy-phenyl)acetic | 357.21 | 358.21 | 358.2 |
| 88 | Val | Val | 3,4-(Methylene-dioxy)phenyl-acetic | 329.17 | 330.17 | 330.2 |
| 89 | Val | Val | 2-Methoxy-cinnamic | 339.19 | 340.19 | |
| 90 | Val | Val | 3,4-(Methylene-dioxy)cinnamic | 353.17 | 354.17 | |
| 91 | Val | Val | 2-Hydroxy-cinnamic | 325.18 | 326.18 | |
| 92 | Val | Val | Benzoic | 283.17 | 284.17 | 284.2 |
| 93 | Val | Val | 4-Chloro-cinnamic | 343.15 | 344.15 | 344.2 |
| 94 | Val | Val | m-Anisic | 313.18 | 314.18 | |
| 95 | Val | Val | 4-Isopropyl-benzoic | 325.22 | 326.22 | 326.2 |

-continued

![Structure I: imidazolinone fused with imidazole, substituents R1, R2, R3]

I

| Pool # | R¹ | R² | R³ (Acid) | MW (calc) | M + H (calc) | Single major peak (MW) found |
|---|---|---|---|---|---|---|
| 96 | Val | Val | 4-Vinylbenzoic | 309.18 | 310.18 | |
| 97 | Val | Val | 4-Fluoro-benzoic | 301.16 | 302.16 | 302.2 |
| 98 | Val | Val | 4-Bromo-benzoic | 361.1 | 362.10 | |
| 99 | Val | Val | 3,4-Dimethoxy-cinnamic | 369.21 | 370.21 | |
| 100 | Val | Val | 4-Hydroxy-benzoic | 299.16 | 300.16 | |
| 101 | Val | Val | trans-Cinnamic | 309.18 | 310.18 | 310.2 |
| 102 | Val | Val | 3,4-Dimethyl-benzoic | 311.2 | 312.20 | 312.2 |
| 103 | Val | Val | 3-Fluoro-4-methylbenzoic | 315.17 | 316.17 | |
| 104 | Val | Val | 3-Bromo-4-methylbenzoic | 375.11 | 376.11 | 376.1 |
| 105 | Val | Val | 3-Iodo-4-methylbenzoic | 423.08 | 424.08 | |
| 106 | Val | Val | 3,4-Dichloro-benzoic | 351.09 | 352.09 | |
| 107 | Val | Val | 4-Biphenyl-carboxylic | 373.22 | 374.22 | 374.2 |
| 108 | Val | Val | 3,4-Difluoro-benzoic | 319.15 | 320.15 | |
| 109 | Val | Val | m-Toluic | 297.18 | 298.18 | 298.2 |
| 110 | Val | Val | Phenylacetic | 297.18 | 298.18 | 298.2 |
| 111 | Val | Val | Hydrocinnamic | 311.2 | 312.20 | 312.2 |
| 112 | Val | Val | 3-Methoxy-4-methylbenzoic | 327.42 | 328.42 | 328.2 |
| 113 | Val | Val | 4-Phenylbutyric | 325.22 | 326.22 | 326.2 |
| 114 | Val | Val | 4-Butylbenzoic | 339.23 | 340.23 | 340.2 |
| 115 | Val | Val | 3,5-Dimethyl-benzoic | 311.2 | 312.20 | 312.2 |
| 116 | Val | Val | 3,5-Bis-(Trifluoro-methyl)benzoic | 419.14 | 420.14 | |
| 117 | Val | Val | 3,4-Dimethoxy-benzoic | 343.19 | 344.19 | |
| 118 | Val | Val | 4-Ethyl-4-biphenyl-carboxylic | 387.23 | 388.23 | |
| 119 | Val | Val | 3,4,5-Tri-methoxybenzoic | 373.2 | 374.20 | |
| 120 | Val | Val | 3,4,5-Tri-ethoxy-benzoic | 415.25 | 416.25 | 416.2 |
| 121 | Val | Val | Butyric | 249.18 | 250.18 | 250.2 |
| 122 | Val | Val | Heptanoic | 291.23 | 292.23 | 292.2 |
| 123 | Val | Val | Isobutyric | 249.18 | 250.18 | 250.2 |
| 124 | Val | Val | (+/−)-2-Methyl-butyric | 263.2 | 264.20 | 264.2 |
| 125 | Val | Val | Isovaleric | 263.2 | 264.20 | 264.2 |
| 126 | Val | Val | 3-Methylvaleric | 277.22 | 278.22 | 278.2 |
| 127 | Val | Val | 4-Methylvaleric | 277.22 | 278.22 | 278.2 |
| 128 | Val | Val | (+/−)-2-Ethyl-hexanoic | 305.25 | 306.25 | 306.2 |
| 129 | Val | Val | Crotonic | 247.17 | 248.17 | |
| 130 | Val | Val | Vinylacetic | 247.17 | 248.17 | 248.2 |
| 131 | Val | Val | trans-3-Hexenoic | 275.2 | 276.20 | 276.3 |
| 132 | Val | Val | 2-Ethyl-2-hexenoic | 303.23 | 304.23 | 304.2 |
| 133 | Val | Val | p-Toluic | 297.18 | 298.18 | 298.2 |
| 134 | Val | Val | p-Anisic | 313.18 | 314.18 | 314.2 |
| 135 | Val | Val | Trimethylacetic | 263.2 | 264.20 | 264.1 |
| 136 | Val | Val | tert-Butylacetic | 277.22 | 278.22 | 278.2 |
| 137 | Val | Val | Cyclohexane-carboxylic | 289.22 | 290.22 | 290.2 |
| 138 | Val | Val | Cyclohexyl-acetic | 303.23 | 304.23 | 304.3 |
| 139 | Val | Val | Dicyclohexyl-acetic | 385.31 | 386.31 | 386.4 |
| 140 | Val | Val | Cyclohexane-butyric | 331.26 | 332.26 | 332.3 |
| 141 | Val | Val | Cycloheptane-carboxylic | 303.23 | 304.23 | |
| 142 | Val | Val | Acetic | 221.15 | 222.15 | 222.2 |
| 143 | Val | Val | 2-Methyl-cyclopropane-carboxylic | 261.18 | 262.18 | |
| 144 | Val | Val | Cyclobutane-carboxylic | 261.18 | 262.18 | 262.2 |
| 145 | Val | Val | Cyclopentane-carboxylic | 275.2 | 276.20 | 276.2 |
| 146 | Val | Val | 3-Cyclopentyl-propionic | 303.23 | 304.23 | 304.2 |
| 147 | Val | Val | 2-Furoic | 273.15 | 274.15 | |
| 148 | Val | Val | Cyclohexane-propionic | 317.25 | 318.25 | 318.3 |
| 149 | Val | Val | 4-Methyl-1-cyclohexane-carboxylic | 303.23 | 304.23 | |
| 150 | Val | Val | 4-tert-Butyl-cyclohexane-carboxylic | 345.28 | 346.28 | |
| 151 | Val | Val | 1-Adamantane-carboxylic | 355.26 | 356.26 | |
| 152 | Val | Val | 4-Methylcyclo-hexaneacetic | 317.25 | 318.25 | 318.2 |
| 153 | Val | Val | 2,4-Hexadienoic | 273.18 | 274.18 | |
| 154 | Val | Val | Tiglic | 261.18 | 262.18 | |
| 155 | Val | Val | 2-Norbornane-acetic | 315.23 | 316.23 | 316.2 |
| 156 | Val | Val | 1-Adamantane-acetic | 355.26 | 356.26 | 356.3 |
| 157 | Val | Val | 2-Ethylbutyric | 277.22 | 278.22 | 278.2 |
| 158 | Val | Val | 2-Thiophene-carboxylic | 351.09 | 352.09 | |

NMR product data for individual compounds from five syntheses carried out following the reaction route outlined above are provided below for compounds corresponding in structure to compound 4b of Scheme 1. Those compounds are referred to as compounds 4b$^{1-5}$.

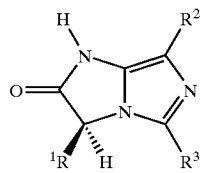

4b$^{1-5}$

Product data:
  4 b$^1$: $^1$H NMR (500 MHz, CD$_3$OD) δ 6.85–7.27 (m, 10H), 5.25–5.35 (t, 1H), 3.75–3.85 (s, 2H), 3.4–3.6 (dd, 2H), 2.57

(s, 3H); HRMS (FAB) m/z 318.1590 found (M+H)+, 318.1606 calculated for $C_{20}H_{20}N_3O^+$.

4b²: ¹H NMR (500 MHz, CD₃OD) δ 4.85–4.95 (m, 1H), 2.60 (s, 3H), 2.54–2.59 (m, 1H), 2.23 (s, 1H), 1.25–1.26 (d, 3H), 0.89–0.90 (d, 3H); HRMS (FAB) m/z 193.1214 found (M)+, 193.1215 calculated for $C_{10}H_{15}N_3O$.

4b³: ¹H NMR (500 MHz, CD₃OD) δ 7.15–7.41 (m, 5H), 4.8–5.0 (m, 2H), 3.97 (s, 2H) 2.59 (s, 3H), 1.27–1.28 (d, 3H), 0.90–0.92 (d, 3H); HRMS (FAB) m/z 269.1528 found (M)+, 269.1528 calculated for $C_{16}H_{19}N_3O$.

4b⁴: ¹H NMR (500 MHz, CD₃OD) δ 5.64 (s, 1H), 4.14 (s, 3H), 3.30 (s, 1H), 2.43 (s, 3H), 1.85–1.90 (dd, 6H); HRMS (FAB) m/z 193.1207 found (M)+, 193.1215 calculated for $C_{10}H_{15}N_3O$.

4b⁵: ¹H NMR (500 MHz, CD₃OD) δ 5.59–5.72 (m, 2H), 5.18–5.20 (d, 1H), 2.68–2.85 (m, 3H), 2.44 (d, 3H), 2.37 (s, 1H), 1.0–1.1 (dd, 6H). LCMS (ES) m/z 208.1 found [M+H]+, 208.14 calculated for $C_{11}H_{18}N_3O^+$.

| Compound | R¹ | R² | R³ |
|---|---|---|---|
| 4b¹ | benzyl | benzyl | methyl |
| 4b² | 2-propyl | methyl | methyl |
| 4b³ | 2-propyl | benzyl | methyl |
| 4b⁴ | methyl | 2-propyl | methyl |
| 4b⁵ | benzyl | benzyl | 2-propyl |

EXAMPLE 2

Binding Inhibition of the Rat Brain Mu Receptor by [3,5,7]-1H-Imidazo[1,5-a]-imidazol-2(3H)-one Compounds The previously prepared [3,5,7]-1H-imidazo[1,5-a]-imidazol-2(3H)-one library of individual compounds was screened for the ability to inhibit the binding of [³H] [D-Ala² MePhe⁴ Gly⁵-ol]enkephalin (DAMGO) that is known to bind specifically to the mu opiate receptor present in rat brain homogenates following literature procedures. [Dooley et al., Science, 266:2019(1994); U.S. Pat. No. 5,763,193.]

Preparation of rat brain membranes and the receptor binding assay were carried out as described in Dooley et al., Life Sci., 52:1509(1993). Each tube in the screening assay contained 0.08 mg of compound mixture per milliliter, 0.5 mL of membrane suspension (0.1 mg of protein), 7 nM ³H-labeled DAMGO [specific activity 36 Ci/mmol, obtained from the National Institute on Drug Abuse (NIDA) repository through Chiron Mimotopes PeptideSystems (San Diego, Calif.) and 50 mL of peptide mixture in 50 mM Tris-HCl buffer (pH 7.4). The final volume was 0.65 mL. The results of these screenings are shown in the table, below, wherein the "R" groups are as discussed for Example 1. The results are reported as percent inhibition of DAMGO binding.

[3,5,7]-1H-Imidazo[1,5-a]imidazol-2(3H)-one Compound Binding Inhibition of [³H]DAMGO

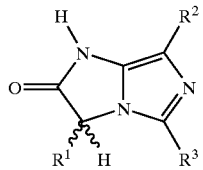

| Pool # | R¹ | R² | R³ | Mean | Minus NSB* | % Bound | % Inhibition |
|---|---|---|---|---|---|---|---|
| 3 | Val | Val | Acetic Acid | 974.05 | 666.05 | 70 | 30 |
| 4 | Leu | Val | Acetic Acid | 980.1 | 672.10 | 70 | 30 |
| 5 | Ileu | Val | Acetic Acid | 1052.8 | 744.80 | 78 | 22 |
| 11 | Nle | Val | Acetic Acid | 756.05 | 448.05 | 47 | 53 |
| 12 | Nva | Val | Acetic Acid | 998.7 | 690.70 | 72 | 28 |
| 18 | Ala | Val | Acetic Acid | 989.15 | 681.15 | 71 | 29 |
| 19 | Val | Val | Acetic Acid | 1027.75 | 719.75 | 75 | 25 |
| 20 | Leu | Val | Acetic Acid | 787.6 | 479.60 | 50 | 50 |
| 21 | Ileu | Val | Acetic Acid | 833.5 | 525.50 | 55 | 45 |
| 27 | Nle | Val | Acetic Acid | 871.25 | 563.25 | 59 | 41 |
| 28 | Nva | Val | Acetic Acid | 932.9 | 624.90 | 66 | 34 |
| 29 | Cha | Val | Acetic Acid | 891.65 | 583.65 | 61 | 39 |
| 30 | Phe | Val | Acetic Acid | 929.9 | 621.90 | 65 | 35 |
| 34 | Val | Gly | Acetic Acid | 956.4 | 648.40 | 68 | 32 |
| 35 | Val | Ala | Acetic Acid | 753.5 | 445.50 | 47 | 53 |
| 36 | Val | Val | Acetic Acid | 940.6 | 632.60 | 66 | 34 |
| 37 | Val | Leu | Acetic Acid | 932.9 | 624.90 | 66 | 34 |
| 38 | Val | Ileu | Acetic Acid | 687.75 | 379.75 | 40 | 60 |
| 39 | Val | Ser | Acetic Acid | | | | |
| 41 | Val | Lys | Acetic Acid | 858.1 | 550.10 | 58 | 42 |
| 42 | Val | Arg | Acetic Acid | 581.65 | 273.65 | 29 | 71 |
| 44 | Val | Nle | Acetic Acid | 947.55 | 639.55 | 67 | 33 |
| 45 | Val | Nv | Acetic Acid | 902.55 | 594.55 | 62 | 38 |
| 46 | Val | Ch | Acetic Acid | 881.4 | 573.40 | 60 | 40 |
| 47 | Val | Ph | Acetic Acid | 897.8 | 589.80 | 62 | 38 |
| 48 | Val | Tyr | Acetic Acid | 728.5 | 420.50 | 44 | 56 |
| 51 | Val | Ala | Acetic Acid | 902.75 | 594.75 | 62 | 38 |
| 52 | Val | Val | Acetic Acid | 959.85 | 651.85 | 68 | 32 |
| 53 | Val | Leu | Acetic Acid | 988.95 | 680.95 | 71 | 29 |
| 54 | Val | Ileu | Acetic Acid | 815.2 | 507.20 | 53 | 47 |

-continued

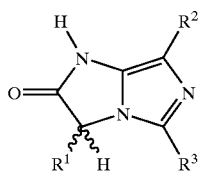

| Pool # | R¹ | R² | R³ | Mean | Minus NSB* | % Bound | % Inhibition |
|---|---|---|---|---|---|---|---|
| 59 | Val | Met | Acetic Acid | 874.75 | 566.75 | 59 | 41 |
| 60 | Val | Nle | Acetic Acid | 902.8 | 594.80 | 62 | 38 |
| 61 | Val | Nva | Acetic Acid | 677.65 | 369.65 | 39 | 61 |
| 62 | Val | Cha | Acetic Acid | 805 | 497.00 | 52 | 48 |
| 63 | Val | Phe | Acetic Acid | 854.35 | 546.35 | 57 | 43 |
| 64 | Val | Tyr | Acetic Acid | 710.9 | 402.90 | 42 | 58 |
| 67 | Val | Val | 1-Phenyl-1-cyclopropanecarboxylic Acid | 830 | 522.00 | 55 | 45 |
| 68 | Val | Val | 2-Phenylbutyric Acid | 935.45 | 627.45 | 66 | 34 |
| 69 | Val | Val | 3-Phenylbutyric Acid | 900.1 | 592.10 | 62 | 38 |
| 70 | Val | Val | m-Tolylacetic Acid | 954.15 | 646.15 | 68 | 32 |
| 71 | Val | Val | 3-Fluorophenylacetic Acid | 853.7 | 545.70 | 57 | 43 |
| 72 | Val | Val | 3-Bromophenylacetic Acid | 563 | 255.00 | 27 | 73 |
| 73 | Val | Val | (α,α,α-Trifluoro-m-tolyl)acetic Acid | 967.25 | 659.25 | 69 | 31 |
| 74 | Val | Val | p-Tolylacetic Acid | 858.65 | 550.65 | 58 | 42 |
| 75 | Val | Val | 4-Fluorophenylacetic Acid | 758.2 | 450.20 | 47 | 53 |
| 76 | Val | Val | 3-Methoxyphenylacetic Acid | 854 | 546.00 | 57 | 43 |
| 77 | Val | Val | 4-Bromophenylacetic Acid | 682.95 | 374.95 | 39 | 61 |
| 78 | Val | Val | 4-Methoxyphenylacetic Acid | 775.2 | 467.20 | 49 | 51 |
| 79 | Val | Val | 4-Ethoxyphenylacetic Acid | 929.1 | 621.10 | 65 | 35 |
| 81 | Val | Val | 3,4-Diclhlorophenylacetic Acid | 988.3 | 680.30 | 71 | 29 |
| 82 | Val | Val | 3,5-Bis-(Trifluoromethyl)-phenylacetic Acid | 911.65 | 603.65 | 63 | 37 |
| 84 | Val | Val | 4-Biphenylacetic Acid | 850.4 | 542.40 | 57 | 43 |
| 87 | Val | Val | (3,4-Dimethoxyphenyl)acetic Acid | 870.35 | 562.35 | 59 | 41 |
| 88 | Val | Val | 3,4-(Methylenedioxy)-cinnamic Acid | | | | |
| 107 | Val | Val | 4-Biphenylcarboxylic Acid | 804.2 | 496.20 | 52 | 48 |
| 110 | Val | Val | Phenylacetic Acid | 818.7 | 510.70 | 54 | 46 |
| 113 | Val | Val | 4-Phenylbutyric Acid | 716.3 | 408.30 | 43 | 57 |
| 121 | Val | Val | Butyric Acid | 826.45 | 518.45 | 54 | 46 |
| 122 | Val | Val | Heptanoic Acid | 817.3 | 509.30 | 53 | 47 |
| 123 | Val | Val | Isobutyric Acid | 832.5 | 524.50 | 55 | 45 |
| 124 | Val | Val | (+/−)-2-Methylbutyric Acid | 901.85 | 593.85 | 62 | 38 |
| 125 | Val | Val | Isovaleric Acid | 763.7 | 455.70 | 48 | 52 |
| 126 | Val | Val | 3-Methylvaleric Acid | 918.7 | 610.70 | 64 | 36 |
| 127 | Val | Val | 4-Methylvaleric Acid | 909.6 | 601.60 | 63 | 37 |

-continued

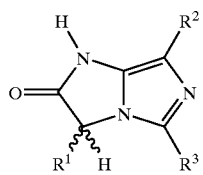

| Pool # | R¹ | R² | R³ | Mean | Minus NSB* | % Bound | % Inhibition |
|---|---|---|---|---|---|---|---|
| 128 | Val | Val | (+/-)-2-Ethylhexanoic Acid | 881.35 | 573.35 | 60 | 40 |
| 135 | Val | Val | Trimethylacetic Acid | 931.85 | 623.85 | 65 | 35 |
| 136 | Val | Val | tert-Butylacetic Acid | 991 | 683.00 | 72 | 28 |
| 137 | Val | Val | Cyclohexane-carboxylic Acid | 933.35 | 625.35 | 66 | 34 |
| 138 | Val | Val | Cycloexylacetic Acid | 877.8 | 569.80 | 60 | 40 |
| 139 | Val | Val | Dicyclo-hexylacetic Acid | 928.85 | 620.85 | 65 | 35 |
| 140 | Val | Val | Cycloheptane-carboxyic Acid | 615.55 | 307.55 | 32 | 68 |
| 142 | Val | Val | Acetic Acid | 946.05 | 638.05 | 67 | 33 |
| 144 | Val | Val | Cyclobutane-carboxylic Acid | 867.3 | 559.30 | 59 | 41 |
| 145 | Val | Val | Cyclopentane-carboxylic Acid | 986.9 | 678.90 | 71 | 29 |
| 146 | Val | Val | 3-Cyclopentyl-propionic Acid | 945.85 | 637.85 | 67 | 33 |
| 148 | Val | Val | Cyclohexane-propionic Acid | 890.8 | 582.80 | 61 | 39 |
| 152 | Val | Val | 4-Methyl-cyclo-hexaneacetic Acid | 770.1 | 462.10 | 48 | 52 |
| 155 | Val | Val | 2-Norbornane-acetic Acid | 918.35 | 610.35 | 64 | 36 |
| 156 | Val | Val | 1-Adamantane-acetic Acid | 925.85 | 617.85 | 65 | 35 |
| 157 | Val | Val | 2-Thiophene-carboxylic Acid | 930.35 | 622.35 | 65 | 35 |

*NSB = non-specific binding.

EXAMPLE 3

Binding Inhibition of the Guinea Pig Brain Kappa Receptor by [3,5,7]-1H-Imidazo[1,5-a]imidazol-2(3H)-one Compounds The above-prepared library of individual compounds was screened for the ability to inhibit the binding of tritiated Compound U69,593 that is known to bind specifically to the kappa opiate receptor present in guinea pig brain homogenates following literature procedures. [Dooley et al., *J. Biol. Chem*, 273(30) 18848–18856 (1998)]

Briefly, guinea pig cortices and cerebella were homogenized in 40 mL of Buffer A [50 mM Tris-HCl, pH 7.4] at 4° C. Homogenates were centrifuged [Beckman® J2-HC, 35,300× g] for 10 minutes. The pellets were resuspended in fresh buffer and incubated at 37° C. for 40 minutes. Following incubation, the suspensions were centrifuged as before, the resulting pellets resuspended in 100 volumes of Tris buffer, and the suspensions combined. Membrane suspensions were prepared and used on the same day. Protein content of the crude homogenates was determined by the method of Bradford, *Anal. Biochem.*, 72:248–252 (1976).

Each assay tube contained 0.5 mL of membrane suspension, 3 nm of tritiated Compound U69,593 [(5a,7a,8b)-(−)-N-methyl-N-(7-(1-pyrrolidinyl)-1-oxaspiro(4,5) dec-8-yl)-benzeneacetamide; Lahti et al., *European J. Pharmacol.*, 109:281–284(199-85)] in a total volume of 0.65 mL. Assay tubes were incubated for 2.5 hours a 25° C. The assay was then filtered through GF-B filters on a Tomec™ harvester (Orange, Conn.). The filters were subsequently washed with 6 mL of 50 mM Tris-HCl, pH 7.4 at 4° C. Bound radioactivity was counted on a Wallace™ Beta-plate Liquid Scintillation Counter (Piscataway, N.J.). Unlabeled U50,488 [(trans-(dl)-3,4-dichloro-N-methyl-N-[2-(1-pyrrolidinyl)-cyclohexyl]-benzeneacetamide) methane sulfonate hydrate; Lahti et al., *Life Sci.*, 31:2257-xx (1982) and Von Voightlander et al., *J. Pharmacol. Exp. Ther.*, 224:7 (1983)]was used as a competitive inhibitor to generate a standard curve and determine nonspecific binding. The results of these assays are shown in the table, below, wherein the "R" groups are as discussed for Example 1.

[3,5,7]-1H-Imidazo[1,5-a]imidazol-2(3H)-one
Compound Binding Inhibition of [³H]U69,593

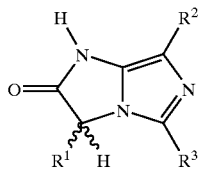

| Pool # | R¹ | R² | R³ | Mean | Minus NSB | % Bound | % Inhibition |
|---|---|---|---|---|---|---|---|
| 3 | Val | Val | Acetic Acid | 1468.8 | 561.80 | 54.228 | 45.772 |
| 4 | Leu | Val | Acetic Acid | 1895.55 | 988.55 | 95.420 | 4.580 |
| 5 | Ileu | Val | Acetic Acid | 1684.45 | 777.45 | 75.043 | 24.957 |
| 11 | Nle | Val | Acetic Acid | 1736.15 | 829.15 | 80.034 | 19.966 |
| 12 | Nva | Val | Acetic Acid | 1680.95 | 773.95 | 74.706 | 25.294 |
| 18 | Ala | Val | Acetic Acid | 1818.85 | 911.85 | 88.016 | 11.984 |
| 19 | Val | Val | Acetic Acid | 1783.25 | 876.25 | 84.580 | 15.420 |
| 20 | Leu | Val | Acetic Acid | 1621.8 | 714.80 | 68.996 | 31.004 |
| 21 | Ileu | Val | Acetic Acid | 1496.7 | 589.70 | 56.921 | 43.079 |
| 27 | Nle | Val | Acetic Acid | 1734.3 | 827.30 | 79.855 | 20.145 |
| 28 | Nva | Val | Acetic Acid | 1607.35 | 700.35 | 67.601 | 32.399 |
| 29 | Cha | Val | Acetic Acid | 1821.55 | 914.55 | 88.277 | 11.723 |
| 30 | Phe | Val | Acetic Acid | 1682.8 | 775.80 | 74.884 | 25.116 |
| 34 | Val | Gly | Acetic Acid | 1726.65 | 819.65 | 79.117 | 20.883 |
| 35 | Val | Ala | Acetic Acid | 1711.9 | 804.90 | 77.693 | 22.307 |
| 36 | Val | Val | Acetic Acid | 1787.35 | 880.35 | 84.976 | 15.024 |
| 37 | Val | Leu | Acetic Acid | 1559.4 | 652.40 | 62.973 | 37.027 |
| 38 | Val | Ileu | Acetic Acid | 1618.1 | 711.10 | 68.639 | 31.361 |
| 39 | Val | Ser | Acetic Acid | 1723.65 | 816.65 | 78.827 | 21.173 |
| 41 | Val | Lys | Acetic Acid | 1444.2 | 537.20 | 51.853 | 48.147 |
| 42 | Val | Arg | Acetic Acid | 1406.35 | 499.35 | 48.200 | 51.800 |
| 44 | Val | Nle | Acetic Acid | 2049.7 | 1142.70 | 110.299 | −10.299 |
| 45 | Val | Nv | Acetic Acid | 1790.45 | 883.45 | 85.275 | 14.725 |
| 46 | Val | Ch | Acetic Acid | 2169 | 1262.00 | 121.815 | −21.815 |
| 47 | Val | Ph | Acetic Acid | 1989.3 | 1082.30 | 104.469 | −4.469 |
| 48 | Val | Tyr | Acetic Acid | 1784 | 877.00 | 84.653 | 15.347 |
| 51 | Val | Ala | Acetic Acid | 1645.8 | 738.80 | 71.313 | 28.687 |
| 52 | Val | Val | Acetic Acid | 1681.35 | 774.35 | 74.744 | 25.256 |
| 53 | Val | Leu | Acetic Acid | 2008.85 | 1101.85 | 106.356 | −6.356 |
| 54 | Val | Ileu | Acetic Acid | 1947.25 | 1040.25 | 100.410 | −0.410 |
| 59 | Val | Met | Acetic Acid | 1724.95 | 817.95 | 78.953 | 21.047 |
| 60 | Val | Nle | Acetic Acid | 1755.4 | 848.40 | 81.892 | 18.108 |
| 61 | Val | Nva | Acetic Acid | 1433.75 | 526.75 | 50.845 | 49.155 |
| 62 | Val | Cha | Acetic Acid | 1776.3 | 869.30 | 83.909 | 16.091 |
| 63 | Val | Phe | Acetic Acid | 1786.7 | 879.70 | 84.913 | 15.087 |
| 64 | Val | Tyr | Acetic Acid | 1545.5 | 638.50 | 61.631 | 38.369 |
| 67 | Val | Val | 1-Phenyl-1-cyclo propanecarboxylic Acid | 1784.1 | 877.10 | 84.662 | 15.338 |
| 68 | Val | Val | 2-Phenylbutyric Acid | 2013.3 | 1106.30 | 106.786 | −6.786 |
| 69 | Val | Val | 3-Phenylbutyric Acid | 1602.75 | 695.75 | 67.157 | 32.843 |
| 70 | Val | Val | m-Tolylacetic Acid | 2019.55 | 1112.55 | 107.389 | −7.389 |
| 71 | Val | Val | 3-Fluoro-phenylacetic Acid | 1541.5 | 634.50 | 61.245 | 38.755 |
| 72 | Val | Val | 3-Bromo-phenylacetic Acid | 1588.15 | 681.15 | 65.748 | 34.252 |
| 73 | Val | Val | (α,α,α-Trifluoro-m-tolyl)acetic Acid | 1717.2 | 810.20 | 78.205 | 21.795 |
| 74 | Val | Val | p-Tolylacetic Acid | 1407.25 | 500.25 | 48.287 | 51.713 |
| 75 | Val | Val | 4-Fluoro-phenylacetic Acid | 1643.95 | 736.95 | 71.134 | 28.866 |
| 76 | Val | Val | 3-Methoxy-phenylacetic Acid | 1859.1 | 952.10 | 91.902 | 8.098 |
| 77 | Val | Val | 4-Bromo-phenylacetic Acid | 1670.1 | 763.10 | 73.658 | 26.342 |
| 78 | Val | Val | 4-Methoxy-phenylacetic Acid | 1812.05 | 905.05 | 87.360 | 12.640 |
| 79 | Val | Val | 4-Ethoxy-phenylacetic Acid | 1842.9 | 935.90 | 90.338 | 9.662 |

-continued

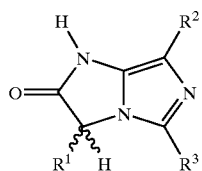

| Pool # | R¹ | R² | R³ | Mean | Minus NSB | % Bound | % Inhibition |
|---|---|---|---|---|---|---|---|
| 81 | Val | Val | 3,4-Diclhloro phenylacetic Acid | 1831.35 | 924.35 | 89.223 | 10.777 |
| 82 | Val | Val | 3,5-Bis-(Trifluoromethyl)-Phenylacetic Acid | 1638.3 | 731.30 | 70.589 | 29.411 |
| 84 | Val | Val | 4-Biphenylacetic Acid | 1628.3 | 721.30 | 69.624 | 30.376 |
| 87 | Val | Val | (3,4-Dimethoxyphenyl)-acetic Acid | 1749.65 | 842.65 | 81.337 | 18.663 |
| 88 | Val | Val | 3,4-(Methylenedioxy)-Cinnamic Acid | 1739.6 | 832.60 | 80.367 | 19.633 |
| 107 | Val | Val | 4-Biphenyl-carboxylic Acid | 2089.6 | 1182.60 | 114.151 | −14.151 |
| 110 | Val | Val | Phenylacetic Acid | 1667.95 | 760.95 | 73.451 | 26.549 |
| 113 | Val | Val | 4-Phenylbutyric Acid | 1545.15 | 638.15 | 61.597 | 38.403 |
| 121 | Val | Val | Butyric Acid | 1533.45 | 626.45 | 60.468 | 39.532 |
| 122 | Val | Val | Heptanoic Acid | 1443.7 | 536.70 | 51.805 | 48.195 |
| 123 | Val | Val | Isobutyric Acid | 1498.8 | 591.80 | 57.124 | 42.876 |
| 124 | Val | Val | (+/−)-2-Methyl-butyric Acid | 1555.85 | 648.85 | 62.630 | 37.370 |
| 125 | Val | Val | Isovaleric Acid | 1553.3 | 646.30 | 62.384 | 37.616 |
| 126 | Val | Val | 3-Methylvaleric Acid | 1666.5 | 759.50 | 73.311 | 26.689 |
| 127 | Val | Val | 4-Methylvaleric Acid | 1592.6 | 685.60 | 66.178 | 33.822 |
| 128 | Val | Val | (+/−)-2-Ethyl-hexanoic Acid | 1503.35 | 596.35 | 57.563 | 42.437 |
| 135 | Val | Val | Trimethylacetic Acid | 1623.6 | 716.60 | 69.170 | 30.830 |
| 136 | Val | Val | tert-Butylacetic Acid | 1741.9 | 834.90 | 80.589 | 19.411 |
| 137 | Val | Val | Cyclohexane-carboxylic Acid | 2249.85 | 1342.85 | 129.619 | −29.619 |
| 138 | Val | Val | Cycloexylacetic Acid | 1639.3 | 732.30 | 70.685 | 29.315 |
| 139 | Val | Val | Dicyclohexyl-acetic Acid | 1515.95 | 608.95 | 58.779 | 41.221 |
| 140 | Val | Val | Cycloheptane-carboxyic Acid | 1424 | 517.00 | 49.903 | 50.097 |
| 142 | Val | Val | Acetic Acid | 1728.8 | 821.80 | 79.324 | 20.676 |
| 144 | Val | Val | Cyclobutane-carboxylic Acid | 1447.5 | 540.50 | 52.172 | 47.828 |
| 145 | Val | Val | Cyclopentane-carboxylic Acid | 1544.15 | 637.15 | 61.501 | 38.499 |
| 146 | Val | Val | 3-Cyclopentyl-propionic Acid | 1622.75 | 715.75 | 69.088 | 30.912 |
| 148 | Val | Val | Cyclohexane-propionic Acid | 1839.1 | 932.10 | 89.971 | 10.029 |
| 152 | Val | Val | 4-Methylcyclo-hexaneacetic Acid | 1515.1 | 608.10 | 58.697 | 41.303 |
| 155 | Val | Val | 2-Norbornane-acetic Acid | 1622.25 | 715.25 | 69.040 | 30.960 |
| 156 | Val | Val | 1-Adamantane-acetic Acid | 1723.4 | 816.40 | 78.803 | 21.197 |
| 157 | Val | Val | 2-Thiophene-carboxylic Acid | 1473.05 | 566.05 | 54.638 | 45.362 |

EXAMPLE 4

Preparation of Libraries of (3,5,7)-1H-Imidazo[1,5-a]imidazol-2(3H)-one Compounds Libraries of [3,5,7]-1H-imidazo[1,5-a]imidazol-2(3H)-one compounds are prepared analogously to the preparation of individual compounds discussed in Example 1. However, whereas a single reagent was used to provide each of the R groups of the intermediates prepared in the syntheses of the individual compounds of Example 1, both single reactants and mixtures of reactants are used to provide the $R^1$, $R^2$ and $R^3$ groups for the different library pools of mixed compounds. As is discussed in treated detail below, 33 library pools are prepared in which $R^1$ is an individual amino acid side chain, with separate pools containing mixtures of 33 amino acids of different side chains ($R^2$) and 92 different carboxylic acid chains ($R^3$).

Where individual reactants are used to provide a particular R group, the procedures of Example 1 are followed. Where mixtures are desired at a particular R group, the protected amino acids or carboxylic acids are provided in mixtures. The mixtures used to provide the various R groups are listed in the table, below, with the relative molar amount of each reactant being listed.

TABLE 4

Mixtures of Reactants Used to Prepare [3,5,7]-1H-Imidazo[1,5-a]imidazol-2(3H)-one Mixed Compound Library

| | Ratio |
|---|---|
| $R^1$ | |
| Boc-amino acids Reagent | |
| Boc-L-Ala | 0.95 |
| Boc-L-Phe | 0.81 |
| Boc-Gly | 1.00 |
| Boc-L-His(DNP) | 0.85 |
| Boc-L-Ile | 1.16 |
| Boc-L-Lys(CBZ) | 1.05 |
| Boc-L-Leu | 1.08 |
| Boc-L-Met | 0.89 |
| Boc-L-Arg(Tos) | 1.42 |
| Boc-L-Ser(Bzl) | 1.30 |
| Boc-L-Thr(Bzl) | 1.60 |
| Boc-L-Val | 1.14 |
| Boc-L-Trp(CHO) | 0.89 |
| Boc-L-Tyr(BrZ) | 1.26 |
| Boc-D-Ala | 0.95 |
| Boc-D-Phe | 0.81 |
| Boc-D-His(DNP) | 0.85 |
| Boc-D-Ile | 1.16 |
| Boc-D-Lys(CBZ) | 1.05 |
| Boc-D-Leu | 1.08 |
| Boc-D-Met | 0.89 |
| Boc-D-Arg(Tos) | 1.42 |
| Boc-D-Ser(Bzl) | 1.30 |
| Boc-D-Thr(Bzl) | 1.60 |
| Boc-D-Val | 1.14 |
| Boc-D-Trp(CHO) | 0.89 |
| Boc-D-Tyr(BrZ) | 1.26 |
| Boc-L-Norvaline | 1.15 |
| Boc-D-Norvaline | 1.15 |
| Boc-L-Norleucine | 1.15 |
| Boc-D-Norleucine | 1.15 |
| Boc-L-Cyclohexylalanine | 1.50 |
| Boc-D-Cyclohexylalanine | 1.50 |
| $R^2$ | |
| Boc-amino acids Reagent | |
| Boc-L-Ala | 0.95 |
| Boc-L-Phe | 0.81 |
| Boc-Gly | 1.00 |
| Boc-L-His(DNP) | 0.85 |
| Boc-L-Ile | 1.16 |
| Boc-L-Lys(CBZ) | 1.05 |
| Boc-L-Leu | 1.08 |
| Boc-L-Met | 0.89 |
| Boc-L-Arg(Tos) | 1.42 |
| Boc-L-Ser(Bzl) | 1.30 |
| Boc-L-Thr(Bzl) | 1.60 |
| Boc-L-Val | 1.14 |
| Boc-L-Trp(CHO) | 0.89 |
| Boc-L-Tyr(BrZ) | 1.26 |
| Boc-D-Ala | 0.95 |
| Boc-D-Phe | 0.81 |
| Boc-D-His(DNP) | 0.85 |
| Boc-D-Ile | 1.16 |
| Boc-D-Lys(CBZ) | 1.05 |
| Boc-D-Leu | 1.08 |
| Boc-D-Met | 0.89 |
| Boc-D-Arg(Tos) | 1.42 |
| Boc-D-Ser(Bzl) | 1.30 |
| Boc-D-Thr(Bzl) | 1.60 |
| Boc-D-Val | 1.14 |
| Boc-D-Trp(CHO) | 0.89 |
| Boc-D-Tyr(BrZ) | 1.26 |
| Boc-L-Norvaline | 1.15 |
| Boc-D-Norvaline | 1.15 |
| Boc-L-Norleucine | 1.15 |
| Boc-D-Norleucine | 1.15 |
| Boc-L-Cyclohexylalanine | 1.50 |
| Boc-D-Cyclohexylalanine | 1.50 |
| $R^3$ | |
| Carboxylic acid Reagent | |
| 1-Phenyl-1-cyclopropanecarboxylic Acid | 1.00 |
| 2-Phenylbutyric Acid | 1.20 |
| 3-Phenylbutyric Acid | 2.60 |
| m-Tolylacetic Acid | 1.80 |
| 3-Fluorophenylacetic Acid | 0.84 |
| 3-Bromophenylacetic Acid | 0.61 |
| (α,α,α-Trifluoro-m-Tolyl)acetic Acid | 0.61 |
| p-Tolylacetic Acid | 1.36 |
| 4-Fluorophenylacetic Acid | 1.04 |
| 3-Methoxyphenylacetic Acid | 1.17 |
| 4-Bromophenylacetic Acid | 0.88 |
| 4-Methoxyphenylacetic Acid | 1.80 |
| 4-Ethoxyphenylacetic Acid | 1.40 |
| 4-Isobutyl-α-methylphenylacetic Acid | 1.70 |
| 3,4-Dichloro-phenylacetic Acid | 0.81 |
| 3,5-Bis-(Trifluoromethyl)phenylacetic Acid | 0.50 |
| 3-(3,4-Dimethoxy-phenyl)propionic Acid | 2.20 |
| 4-Biphenylacetic Acid | 1.40 |
| α-Methylcinnamic Acid | 1.95 |
| 2-(Trifluoromethyl)cinnamic Acid | 1.03 |
| (3,4-Dimethoxyphenyl)acetic Acid | 1.44 |
| 3,4-(Methylenedioxy)phenylacetic Acid | 1.27 |
| 2-Methoxycinnamic Acid | 5.60 |
| 3,4-(Methylenedioxy)cinnamic Acid | 10.40 |
| 2-Hydroxy-cinnamic Acid | 4.90 |
| Benzoic Acid | 1.28 |
| 4-Chlorocinnamic Acid | 2.95 |
| m-Anisic Acid | 1.52 |
| 4-Isopropylbenzoic Acid | 3.00 |
| 4-Vinylbenzoic Acid | 1.50 |
| 4-Fluorobenzoic Acid | 1.22 |
| 4-Bromobenzoic Acid | 0.59 |
| 3,4-Dimethoxycinnamic Acid | 7.27 |
| 4-Hydroxybenzoic Acid | 7.61 |
| trans-Cinnamic Acid | 4.20 |
| 3,4-Dimethylbenzoic Acid | 2.44 |
| 3-Fluoro-4-methylbenzoic Acid | 0.75 |
| 3-Bromo-4-methylbenzoic Acid | 0.86 |
| 3-Iodo-4-methylbenzoic Acid | 0.84 |
| 3,4-Dichlorobenzoic Acid | 0.39 |

TABLE 4-continued

Mixtures of Reactants Used to Prepare [3,5,7]-1H-Imidazo[1,5-a]imidazol-2(3H)-one Mixed Compound Library

| | Ratio |
|---|---|
| 4-Biphenylcarboxylic Acid | 5.10 |
| 3,4-Difluorobenzoic Acid | 0.45 |
| m-Toluic Acid | 1.60 |
| Phenylacetic Acid | 1.00 |
| Hydrocinnamic Acid | 2.50 |
| 3-Methoxy-4-methylbenzoic Acid | 2.10 |
| 4-Phenylbutyric Acid | 3.00 |
| 4-Butylbenzoic Acid | 2.60 |
| 3,5-Dimethylbenzoic Acid | 1.94 |
| 3,5-Bis-(Trifluoromethyl)Benzoic Acid | 0.96 |
| 3,4-Dimethoxybenzoic Acid | 3.08 |
| 4-Ethyl-4-biphenylcarboxylic Acid | 0.92 |
| 3,4,5-Trimethoxybenzoic Acid | 1.46 |
| 3,4,5-Triethoxybenzoic Acid | 2.37 |
| Butyric Acid | 3.39 |
| Heptanoic Acid | 3.51 |
| Isobutyric Acid | 3.11 |
| (+/−)-2-Methylbutyric Acid | 6.25 |
| Isovaleric Acid | 6.36 |
| 3-Methylvaleric Acid | 5.06 |
| 4-Methylvaleric Acid | 3.32 |
| (+/−)-2-Ethylhexanoic Acid | * |
| Crotonic Acid | 5.26 |
| Vinylacetic Acid | 1.30 |
| trans-3-Hexenoic Acid | * |
| 2-Ethyl-2-hexenoic Acid | 11.63 |
| p-Toluic Acid | 2.28 |
| p-Anisic Acid | 5.38 |
| Trimethylacetic Acid | 4.24 |
| tert-Butylacetic Acid | * |
| Cyclohexanecarboxylic Acid | 3.51 |
| Cyclohexylacetic Acid | 3.95 |
| Dicyclohexylacetic Acid | * |
| Cyclohexanebutyric Acid | 3.33 |
| Cycloheptanecarboxylic Acid | 2.60 |
| Acetic Acid | 2.65 |
| 2-Methylcyclopropanecarboxylic Acid | 2.42 |
| Cyclobutanecarboxylic Acid | 2.77 |
| Cyclopentanecarboxylic Acid | 3.03 |
| 3-Cyclopentylpropionic Acid | 3.71 |
| 2-Furoic Acid | 4.44 |
| Cyclohexanepropionic Acid | 2.80 |
| 4-Methyl-1-cyclohexanecarboxylic Acid | 5.92 |
| 4-tert-Butyl-cyclohexanecarboxylic Acid | 6.64 |
| 1-Adamantanecarboxylic Acid | * |
| 4-Methylcyclohexaneacetic Acid | 4.79 |
| 2,4-Hexadienoic Acid | * |
| Tiglic Acid | 4.59 |
| 2-Norbornaneacetic Acid | 5.45 |
| 1-Adamantaneacetic Acid | 11.16 |
| 2-Ethylbutyric Acid | * |
| 2-Thiophenecarboxylic Acid | 1.16 |

*—ratio not determined

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A library of compounds having a structure corresponding to that shown in Formula I, below, or a pharmaceutically acceptable salt thereof:

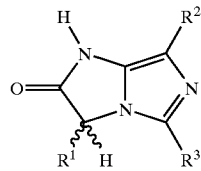

wherein:

$R^1$ and $R^2$ are independently selected from the group consisting of a hydrido, $C_1$–$C_{10}$ alkyl, $C_1$–$C_{10}$ substituted alkyl, $C_7$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group; and $R^3$ is selected from the group consisting of a hydrido, $C_1$–$C_{10}$ alkyl, $C_1$–$C_{10}$ substituted alkyl, $C_2$–$C_{10}$ alkenyl, $C_2$–$C_{10}$ substituted alkenyl, $C_2$–$C_{10}$ alkynyl, $C_2$–$C_{10}$ substituted alkynyl, $C_3$–$C_7$ substituted cycloalkyl, phenyl, $C_7$–$C_{16}$ phenylalkyl, $C_7$–$C_{16}$ phenylalkenyl, $C_7$–$C_{16}$ phenylalkenyl and a $C_7$–$C_{16}$ substituted phenylalkenyl group.

2. The library according to claim 1 wherein $R^1$ and $R^2$ are independently selected from the group consisting of a hydrido, methyl, benzyl, 2-butyl, aminobutyl, N,N-dimethyl-aminobutyl, N-methylaminobutyl, N-methyl-N-benzylaminobutyl, 2-methylpropyl, methylsulfinylethyl, methylthioethyl, N,N-dimethylaminoethyl, N,N-dimethylaminopropyl, N',N',N'-trimethylguanidinopropyl, N',N',N'-tribenzylguanidinopropyl, N',N'-dibenzylguanidinopropyl, N'-methylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and a 4-imidazolyl-methyl substituent.

3. The library according to claim 1 wherein $R^3$ is selected from the group consisting of a 1-phenyl-1-cyclopropyl, 1-phenylbutyl, 2-phenylbutyl, 3-fluorobenzyl, 3-bromobenzyl, α,α,α-trifluoro-m-xylyl, p-xylyl, 4-fluorobenzyl, 3-methoxybenzyl, 4-bromobenzyl, 4-methoxybenzyl, 4-ethoxybenzyl, 4-isobutyl-α-methylbenzyl, 3,4-dichlorobenzyl, 3,5-bis-(trifluoromethyl)benzyl, 2-(3,4-dimethoxyphenyl)ethyl, 4-biphenylmethyl, β-methylstyryl, 2-(trifluoromethyl)-styryl, 3,4-dimethoxybenzyl, 3,4-dihydroxybenzyl, 2-methoxystyryl, 3,4-dihydroxystyryl, 2-hydroxystyryl, phenyl, 4-chlorostyryl, 3-methoxyphenyl, 4-isopropylphenyl, 4-vinylphenyl, 4-fluorophenyl, 4-bromophenyl, 3,4-dimethoxystyryl, 4-hydroxyphenyl, trans-styryl, 3,4-dimethylphenyl, 3-fluoro-4-methylphenyl, 3-bromo-4-methyl-phenyl, 3-iodo-4-methyl-phenyl, 3,4-dichlorophenyl, 4-biphenyl, 3,4-difluorophenyl, m-tolyl, benzyl, phenethyl, 3-methoxy-4-methylphenyl, 3-phenylpropyl, 4-butylphenyl, 3,5-dimethylphenyl, 3,5-bis-(trifluoromethyl)phenyl, 3,4-dimethoxyphenyl, 4-ethyl-4-biphenyl, 3,4,5-triethoxyphenyl, propyl, hexyl, isopropyl, 2-butyl, isobutyl, 2-pentyl, isovaleryl, 3-heptyl, 1-propenyl, 2-propenyl, trans-2-pentenyl, 1-ethyl-1-pentenyl, p-tolyl, p-anisyl, t-butyl, neopentyl, cyclohexyl, cyclohexylmethyl, dicyclohexylmethyl, cyclohexylpropyl, cycloheptyl, methyl, 2-methylcyclopropyl, cyclobutyl, cyclopentyl, cyclopentylethyl, 2-furyl, cyclohexylethyl, 4-methylcyclohexyl, 4-tert-butyl-cyclohexyl, 1-adamantyl, 4-methylcyclohexylmethyl, 1,3-pentadienyl, 2-buten-2-yl, 2-norbornanemethyl, 1-adamantanemethyl, 3-pentyl, and a 2-thiophene substituent.

4. The library according to claim 1 wherein the $R^1$ substituent is a side chain from an amino acid selected from the group consisting of Ala, Phe, Gly, His, Ile, Lys, Leu, Met, Arg, Nva, Ser, Thr, Val, Tyr, Tyr, Nle, Cha, ala, phe, his, ile, lys, leu, met, arg, ser, thr, val, trp, tyr, nle, nva, and cha, wherein amino acids written in all lower case letters are D-amino acids.

5. The library according to claim 1 wherein the $R^2$ substituent is a side chain from an amino acid selected from the group consisting of Ala, Phe, Gly, His, Ile, Lys, Leu, Met, Arg, Nva, Ser, Thr, Val, Tyr, Tyr, Nle, Cha, ala, phe, his, ile, lys, leu, met, arg, ser, thr, val, trp, tyr, nle, nva, and cha, wherein amino acids written in all lower case letters are D-amino acids.

6. A library of compounds having a structure corresponding to that shown in the formula below, or a pharmaceutically acceptable salt thereof:

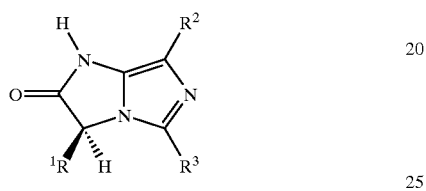

wherein:
$R^1$ and $R^2$ are independently benzyl, methyl or 2-propyl and $R^3$ is methyl or 2-propyl.

7. A library of compounds having a structure corresponding to that shown in Formula I, below, or a pharmaceutically acceptable salt thereof:

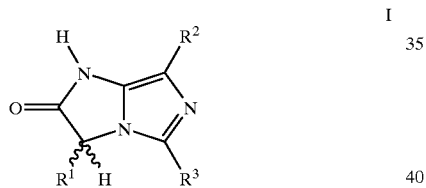

I wherein:
$R^1$ and $R^2$ are independently selected from the group consisting of a hydrido, methyl, benzyl, 2-butyl, aminobutyl, N,N-dimethyl-aminobutyl, N-methylaminobutyl, N-methyl-N-benzylaminobutyl, 2-methylpropyl, methylsulfinylethyl, methylthioethyl, N,N-dimethyl-aminoethyl, N,N-dimethyl-aminopropyl, N',N',N'-trimethylguanidinopropyl, N',N',N'-tribenzylguanidinopropyl, N',N'-dibenzylguanidinopropyl, N'-methylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and a 4-imidazolylmethyl group; and $R^3$ is selected from the group consisting of a 1-phenyl-1-cyclopropyl, 1-phenylbutyl, 2-phenylbutyl, 3-fluorobenzyl, 3-bromobenzyl, α,α,α-trifluoro-m-xylyl, p-xylyl, 4-fluorobenzyl, 3-methoxybenzyl, 4-bromobenzyl, 4-methoxybenzyl, 4-ethoxybenzyl, 4-isobutyl-α-methylbenzyl, 3,4-dichlorobenzyl, 3,5-bis-(trifluoromethyl)benzyl, 2-(3, 4-dimethoxyphenyl)ethyl, 4-biphenylmethyl, β-methylstyryl, 2-(trifluoromethyl) styryl, 3,4-dimethoxybenzyl, 3,4-dihydroxy-benzyl, 2-methoxystyryl, 3,4-dihydroxystyryl, 2-hydroxystyryl, phenyl, 4-chlorostyryl, 3-methoxyphenyl, 4-isopropylphenyl, 4-vinylphenyl, 4-fluorophenyl, 4-bromophenyl, 3,4-dimethoxystyryl, 4-hydroxyphenyl, trans-styryl, 3,4-dimethylphenyl, 3 fluoro-4-methylphenyl, 3-bromo-4-methyl-phenyl, 3-iodo-4-methyl-phenyl, 3,4-dichlorophenyl, 4-biphenyl, 3,4-difluorophenyl, m-tolyl, benzyl, phenethyl, 3-methoxy-4-methylphenyl, 3-phenylpropyl, 4-butylphenyl, 3,5-dimethylphenyl, 3,5-bis-(trifluoromethyl)phenyl, 3,4-dimethoxyphenyl, 4-ethyl-4-biphenyl, 3,4,5-triethoxy-phenyl, propyl, hexyl, isopropyl, 2-butyl, isobutyl, 2-pentyl, isovaleryl, 3-heptyl, 1-propenyl, 2-propenyl, trans-2-pentenyl, 1-ethyl-1-pentenyl, p-tolyl, p-anisyl, t-butyl, neopentyl, cyclohexyl, cyclohexylmethyl, dicyclohexylmethyl, cyclohexylpropyl, cycloheptyl, methyl, 2-methylcyclopropyl, cyclobutyl, cyclopentyl, cyclopentylethyl, 2-furyl, cyclohexylethyl, 4-methylcyclohexyl, 4-tert-butyl-cyclohexyl, 1-adamantyl, 4-methylcyclohexylmethyl, 1,3-pentadienyl, 2-buten-2-yl, 2-norbornanemethyl, 1-adamantanemethyl, 3-pentyl, and a 2-thiophene substituent.

8. The library according to claim 7 wherein the $R^1$ substituent is a side chain from an amino acid selected from the group consisting of Ala, Phe, Gly, His, Ile, Lys, Leu, Met, Arg, Nva, Ser, Thr, Val, Tyr, Tyr, Nle, Cha, ala, phe, his, ile, lys, leu, met, arg, ser, thr, val, trp, tyr, nle, nva, and cha, wherein amino acids written in all lower case letters are D-amino acids.

9. The library according to claim 7 wherein the $R^2$ substituent is a side ham from an amino acid selected from the group consisting of Ala, Phe, Gly, His, Ile, Lys, Leu, Met, Arg, Nva, Ser, Thr, Val, Tyr, Tyr, Nle, Cha, ala, phe, his, ile, lys, leu, met, arg, ser, thr, val, trp, tyr, nle, nva, and cha, wherein amino acids written in all lower case letters are D-amino acids.

* * * * *